(12) United States Patent
Weiner et al.

(10) Patent No.: US 10,792,358 B2
(45) Date of Patent: Oct. 6, 2020

(54) ISG15 AND ITS USE AS AN ADJUVANT

(71) Applicant: The Trustees of the University of Pennsylvania, Philadelphia, PA (US)

(72) Inventors: David Weiner, Merion, PA (US); Daniel Villarreal, San Diego, CA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/559,431

(22) PCT Filed: Mar. 18, 2016

(86) PCT No.: PCT/US2016/023306
§ 371 (c)(1),
(2) Date: Sep. 19, 2017

(87) PCT Pub. No.: WO2016/154071
PCT Pub. Date: Sep. 29, 2016

(65) Prior Publication Data
US 2018/0078638 A1 Mar. 22, 2018

Related U.S. Application Data

(60) Provisional application No. 62/136,325, filed on Mar. 20, 2015.

(51) Int. Cl.
*A61K 39/39* (2006.01)
*A61P 31/12* (2006.01)
*A61P 35/00* (2006.01)
*A61K 39/12* (2006.01)
*A61K 39/015* (2006.01)
*A61K 39/04* (2006.01)
*A61K 39/00* (2006.01)

(52) U.S. Cl.
CPC .......... *A61K 39/39* (2013.01); *A61K 39/0011* (2013.01); *A61K 39/015* (2013.01); *A61K 39/04* (2013.01); *A61K 39/12* (2013.01); *A61P 31/12* (2018.01); *A61P 35/00* (2018.01); *A61K 2039/53* (2013.01); *A61K 2039/555* (2013.01); *A61K 2039/55516* (2013.01); *A61K 2039/585* (2013.01); *C12N 2710/20034* (2013.01); *C12N 2740/00034* (2013.01); *C12N 2760/16034* (2013.01); *Y02A 50/412* (2018.01)

(58) Field of Classification Search
None
See application file for complete search history.

(56) References Cited

U.S. PATENT DOCUMENTS

| | | |
|---|---|---|
| 7,655,249 B2 | 2/2010 | Gaiger |
| 2006/0216722 A1 | 9/2006 | Betsholtz |
| 2007/0042945 A1* | 2/2007 | Bodary ............... C07K 14/47 536/23.2 |
| 2010/0111986 A1 | 5/2010 | Scheinberg |
| 2010/0285061 A1 | 11/2010 | Felber |
| 2010/0292160 A1 | 11/2010 | Sugiyama |
| 2011/0070251 A1 | 3/2011 | Sugiyama |
| 2011/0305724 A1* | 12/2011 | Paterson ............ A61K 31/711 424/200.1 |

FOREIGN PATENT DOCUMENTS

| | | | |
|---|---|---|---|
| EP | 0451550 A2 * | 10/1991 | .......... C07K 14/005 |
| JP | 2007106716 A * | 4/2007 | |
| WO | 2010020676 A1 | 2/2010 | |

OTHER PUBLICATIONS

Laurence M Wood et al: "The ubiquitin-like protein, ISG15, is a novel tumor-associated antigen for cancer immunotherapy", Cancer Immunology,Immunotherapy, Springer,Berlin, DE, vol. 61, No. 5, Nov. 6, 2011 (Nov. 6, 2011), pp. 689-700.
Villarreal et al: "Immunoadjuvant ISG15 enhances human papillomavirus 16 antigen-specific cell-mediated antitumor immunity", Cancer Research, American Association for Cancer Research, US vol. 74, No. 19 Oct. 1, 2014 (Oct. 1, 2014), pp. LB-257, Retrieved from the Internet: URL:http://cancerres.aacrjournals.org/contenu74/19_Supplement/LB-257.short.
Genbank, Database accession No. CT010333.1, URL: genbank, XP055317687 [A] 2-3, (18-27)/2, 28-32 * , mRNA sequence *, 2005.
Villarreal et al., "Immunoadjuvant ISG15 enhances human papillomavirus 16 antigen-specific cell-mediated antitumor immunity.", Proceedings of the 105th Annual Meeting of the American Association for Cancer Research ;, San Diego , CA . Philadelphia (PA, vol. 74, No. 19, (Oct. 1, 2014), URL: http://cancerres.aacrjournals.org/contenU74/19_Supplement/LB-257.short, (Aug. 1, 2016), 1 page.
Villarreal D, et al. Alarmin IL-33 acts as an immunoadjuvant to enhance antigen-specific tumor immunity. Cancer Res 2014;74:1789-800.
Shedlock DJ, et al. Induction of broad cytotoxic T cells by protective DNA vaccination against marburg and ebola. Mol Ther 2013;21:1432-1444.
Yan J, et al., Induction of antitumor immunity in vivo following delivery of a novel HPV-16 DNA vaccine encoding an E6/E7 fusion antigen. Vaccine 2009;27:431-40.
Shedlock, D.J., et al., A highly optimized DNA vaccine confers complete protective immunity against high-dose lethal lymphocytic choriomeningitis virus challenge. Vaccine, 2011. 29(39): p. 6755-62.

(Continued)

*Primary Examiner* — Oluwatosin A Ogunbiyi
(74) *Attorney, Agent, or Firm* — Riverside Law LLP

(57) ABSTRACT

Disclosed herein is a vaccine comprising an antigen and ISG15. Also disclosed herein is a method for increasing an immune response in a subject in need thereof. Further disclosed herein is a method for treating a subject in need thereof. The methods may comprise administering the vaccine to the subject.

16 Claims, 8 Drawing Sheets
Specification includes a Sequence Listing.

(56) References Cited

OTHER PUBLICATIONS

Australian Office Action for Application No. 2016235437 dated Apr. 20, 2018, 5 pages.
Indian Examination Report for Application No. 4289/DELNP/2015, dated Nov. 22, 2019, 8 pages.
Haber et al., "Alternative splicing and genomic structure of the Wilms tumor gene WT1", PNAS USA, Nov. 30, 1991, vol. 88, pp. 9618-9622.
Japanese Office Action (with English language translation) for Application No. JP2017-548971, dated Dec. 3, 2019, 9 pages.

* cited by examiner

SEQUENCE LISTING

```
<160> NUMBER OF SEQ ID NOS: 13

<210> SEQ ID NO 1
<211> LENGTH: 534
<212> TYPE: DNA
<213> ORGANISM: Artificial Sequence
<220> FEATURE:
<223> OTHER INFORMATION: mut ISG15 mouse DNA

<400> SEQUENCE: 1
atggactgga cctggattct gttcctcgtc gccgctgcta caagagtgca ttccgcctgg     60
```

```
gacctcaaag tgaagatgct cggggggtaac gacttcctgg tgtcagtcac taatagcatg    120
accgtgtccg agctgaagaa acagatcgca cagaaaattg gcgtcccagc ctttcagcag    180
aggctggccc accagacagc tgtgctccag gatggactga ctctcagctc cctgggcctc    240
ggaccctcta gtaccgtgat gctggtggtc cagaactgct ctgaacctct gagtatcctc    300
gtgaggaacg agagagggca ctctaatatc tacgaagtgt tcctgaccca gacagtcgac    360
acactcaaga aaaaggtgtc ccagcgggag caggtccatg aagaccagtt ctggctgagc    420
tttgagggac gccccatgga ggataaagaa ctgctcgggg aatatggtct gaagccccag    480
tgtaccgtca tcaaacatgc agcagcagca ggtggaggcg agaccagtg tgcc          534

<210> SEQ ID NO 2
<211> LENGTH: 178
<212> TYPE: PRT
<213> ORGANISM: Artificial Sequence
<220> FEATURE:
<223> OTHER INFORMATION: mut ISG15 mouse protein

<400> SEQUENCE: 2

Met Asp Trp Thr Trp Ile Leu Phe Leu Val Ala Ala Ala Thr Arg Val
1               5                   10                  15

His Ser Ala Trp Asp Leu Lys Val Lys Met Leu Gly Gly Asn Asp Phe
                20                  25                  30

Leu Val Ser Val Thr Asn Ser Met Thr Val Ser Glu Leu Lys Lys Gln
            35                  40                  45

Ile Ala Gln Lys Ile Gly Val Pro Ala Phe Gln Gln Arg Leu Ala His
        50                  55                  60

Gln Thr Ala Val Leu Gln Asp Gly Leu Thr Leu Ser Ser Leu Gly Leu
65                  70                  75                  80

Gly Pro Ser Ser Thr Val Met Leu Val Val Gln Asn Cys Ser Glu Pro
                85                  90                  95

Leu Ser Ile Leu Val Arg Asn Glu Arg Gly His Ser Asn Ile Tyr Glu
            100                 105                 110

Val Phe Leu Thr Gln Thr Val Asp Thr Leu Lys Lys Lys Val Ser Gln
        115                 120                 125

Arg Glu Gln Val His Glu Asp Gln Phe Trp Leu Ser Phe Glu Gly Arg
    130                 135                 140

Pro Met Glu Asp Lys Glu Leu Leu Gly Glu Tyr Gly Leu Lys Pro Gln
145                 150                 155                 160

Cys Thr Val Ile Lys His Ala Ala Ala Ala Gly Gly Gly Asp Gln
                165                 170                 175

Cys Ala

<210> SEQ ID NO 3
<211> LENGTH: 534
<212> TYPE: DNA
<213> ORGANISM: Artificial Sequence
<220> FEATURE:
<223> OTHER INFORMATION: wt ISG15 mouse DNA

<400> SEQUENCE: 3
atggactgga catggattct gtttctggtg gcagccgcta ctcgggtgca tagtgcttgg     60
gacctcaaag tgaagatgct cggggggtaac gacttcctgg tgtcagtcac taatagcatg   120
accgtgtccg agctgaagaa acagatcgca cagaaaattg gagtcccagc atttcagcag   180
aggctggcac accagacagc tgtgctccag gatggactga ctctcagctc cctgggcctc   240
```

```
ggaccctcta gtaccgtgat gctggtggtc cagaactgct ctgaacctct gagtatcctc      300
gtgcggaacg agcgcgggca ctctaatatc tacgaagtgt tcctgaccca gacagtcgac      360
acactcaaga aaaggtgtc ccagcgagag caggtccatg aagaccagtt ctggctgagc       420
tttgagggca gaccaatgga ggataaggaa ctgctcgggg aatatggtct gaaaccccag      480
tgcaccgtga tcaagcatct gaggctcaga ggaggaggag gcgaccagtg tgct            534
```

<210> SEQ ID NO 4
<211> LENGTH: 178
<212> TYPE: PRT
<213> ORGANISM: Artificial Sequence
<220> FEATURE:
<223> OTHER INFORMATION: wt ISG15 mouse protein

<400> SEQUENCE: 4

```
Met Asp Trp Thr Trp Ile Leu Phe Leu Val Ala Ala Thr Arg Val
1               5                   10                  15

His Ser Ala Trp Asp Leu Lys Val Lys Met Leu Gly Gly Asn Asp Phe
            20                  25                  30

Leu Val Ser Val Thr Asn Ser Met Thr Val Ser Glu Leu Lys Lys Gln
        35                  40                  45

Ile Ala Gln Lys Ile Gly Val Pro Ala Phe Gln Gln Arg Leu Ala His
    50                  55                  60

Gln Thr Ala Val Leu Gln Asp Gly Leu Thr Leu Ser Ser Leu Gly Leu
65                  70                  75                  80

Gly Pro Ser Ser Thr Val Met Leu Val Val Gln Asn Cys Ser Glu Pro
                85                  90                  95

Leu Ser Ile Leu Val Arg Asn Glu Arg Gly His Ser Asn Ile Tyr Glu
            100                 105                 110

Val Phe Leu Thr Gln Thr Val Asp Thr Leu Lys Lys Lys Val Ser Gln
        115                 120                 125

Arg Glu Gln Val His Glu Asp Gln Phe Trp Leu Ser Phe Glu Gly Arg
    130                 135                 140

Pro Met Glu Asp Lys Glu Leu Leu Gly Glu Tyr Gly Leu Lys Pro Gln
145                 150                 155                 160

Cys Thr Val Ile Lys His Leu Arg Leu Arg Gly Gly Gly Gly Asp Gln
                165                 170                 175

Cys Ala
```

<210> SEQ ID NO 5
<211> LENGTH: 546
<212> TYPE: DNA
<213> ORGANISM: Artificial Sequence
<220> FEATURE:
<223> OTHER INFORMATION: mut ISG15 human vers.1 DNA

<400> SEQUENCE: 5

```
atggactgga cttggattct gtttctggtc gccgctgcta ctcgcgtgca ttctggctgg      60
gacctgactg tgaagatgct ggctggaaac gagttccagg tgtccctgag ctcctctatg     120
agcgtctccg aactgaaggc tcagatcaca cagaaaattg gggtgcacgc ctttcagcag     180
aggctggctg tgcatccttc tggagtcgca ctgcaggacc gagtgccact ggcatctcag     240
ggactgggac caggaagtac tgtgctgctg gtggtcgaca agtgcgatga ccactgtca      300 atcctggtgc ggaacaacaa gggcagaagt tcaacctacg aagtgcgact gacccagaca     360
gtcgcccacc tgaagcagca ggtgagcgga ctggagggag tccaggacga tctgttctgg     420
```

```
ctgacctttg aggggaagcc cctggaagat cagctgcctc tgggagaata tggcctgaaa    480
cccctgtcca ctgtctttat gaatgccaga gccagaggag ccgccactga gccaggggga    540
aggagc                                                               546
```

<210> SEQ ID NO 6
<211> LENGTH: 182
<212> TYPE: PRT
<213> ORGANISM: Artificial Sequence
<220> FEATURE:
<223> OTHER INFORMATION: mut ISG15 human vers.1 protein

<400> SEQUENCE: 6

```
Met Asp Trp Thr Trp Ile Leu Phe Leu Val Ala Ala Thr Arg Val
 1               5                  10                  15

His Ser Gly Trp Asp Leu Thr Val Lys Met Leu Ala Gly Asn Glu Phe
            20                  25                  30

Gln Val Ser Leu Ser Ser Ser Met Ser Val Ser Glu Leu Lys Ala Gln
        35                  40                  45

Ile Thr Gln Lys Ile Gly Val His Ala Phe Gln Gln Arg Leu Ala Val
    50                  55                  60

His Pro Ser Gly Val Ala Leu Gln Asp Arg Val Pro Leu Ala Ser Gln
65                  70                  75                  80

Gly Leu Gly Pro Gly Ser Thr Val Leu Leu Val Val Asp Lys Cys Asp
                85                  90                  95

Glu Pro Leu Ser Ile Leu Val Arg Asn Asn Lys Gly Arg Ser Ser Thr
            100                 105                 110

Tyr Glu Val Arg Leu Thr Gln Thr Val Ala His Leu Lys Gln Gln Val
        115                 120                 125

Ser Gly Leu Glu Gly Val Gln Asp Asp Leu Phe Trp Leu Thr Phe Glu
    130                 135                 140

Gly Lys Pro Leu Glu Asp Gln Leu Pro Leu Gly Glu Tyr Gly Leu Lys
145                 150                 155                 160

Pro Leu Ser Thr Val Phe Met Asn Ala Arg Ala Arg Gly Ala Ala Thr
                165                 170                 175

Glu Pro Gly Gly Arg Ser
            180
```

<210> SEQ ID NO 7
<211> LENGTH: 546
<212> TYPE: DNA
<213> ORGANISM: Artificial Sequence
<220> FEATURE:
<223> OTHER INFORMATION: wt ISG15 human DNA

<400> SEQUENCE: 7

```
atggattgga cttggattct gttcctggtc gctgccgcta ctcgcgtgca ctctggatgg     60
gacctgaccg tgaaaatgct ggctggaaac gagttccagg tgtccctgag ctcctctatg    120
agcgtctccg aactgaaggc tcagatcaca cagaaaattg ggtgcacgc ctttcagcag    180 aggctggctg tgcatccttc tggagtcgca ctgcaggacc gagtgccact ggcatctcag    240
ggactgggac aggaagtac tgtgctgctg gtggtcgaca agtgcgatga gccactgtca    300
atcctggtgc ggaacaacaa gggcagaagt tcaacctacg aagtgcgact gacccagaca    360
gtcgcccacc tgaagcagca ggtgagcgga ctggagggag tccaggacga tctgttctgg    420
ctgacctttg aggggaagcc cctggaagat cagctgcctc tgggagaata tggcctgaaa    480
cccctgagca ctgtctttat gaatctgagg ctgagaggcg ggggaactga acctggaggg    540
``` cggagc 546

<210> SEQ ID NO 8
<211> LENGTH: 182
<212> TYPE: PRT
<213> ORGANISM: Artificial Sequence
<220> FEATURE:
<223> OTHER INFORMATION: wt ISG15 human protein

<400> SEQUENCE: 8

Met Asp Trp Thr Trp Ile Leu Phe Leu Val Ala Ala Ala Thr Arg Val
1               5                   10                  15

His Ser Gly Trp Asp Leu Thr Val Lys Met Leu Ala Gly Asn Glu Phe
            20                  25                  30

Gln Val Ser Leu Ser Ser Ser Met Ser Val Ser Glu Leu Lys Ala Gln
        35                  40                  45

Ile Thr Gln Lys Ile Gly Val His Ala Phe Gln Gln Arg Leu Ala Val
    50                  55                  60

His Pro Ser Gly Val Ala Leu Gln Asp Arg Val Pro Leu Ala Ser Gln
65                  70                  75                  80

Gly Leu Gly Pro Gly Ser Thr Val Leu Leu Val Val Asp Lys Cys Asp
                85                  90                  95

Glu Pro Leu Ser Ile Leu Val Arg Asn Asn Lys Gly Arg Ser Ser Thr
            100                 105                 110

Tyr Glu Val Arg Leu Thr Gln Thr Val Ala His Leu Lys Gln Gln Val
        115                 120                 125

Ser Gly Leu Glu Gly Val Gln Asp Asp Leu Phe Trp Leu Thr Phe Glu
    130                 135                 140

Gly Lys Pro Leu Glu Asp Gln Leu Pro Leu Gly Glu Tyr Gly Leu Lys
145                 150                 155                 160

Pro Leu Ser Thr Val Phe Met Asn Leu Arg Leu Arg Gly Gly Thr
                165                 170                 175

Glu Pro Gly Gly Arg Ser
            180

<210> SEQ ID NO 9
<211> LENGTH: 546
<212> TYPE: DNA
<213> ORGANISM: Artificial Sequence
<220> FEATURE:
<223> OTHER INFORMATION: mut ISG15 human vers.2 DNA

<400> SEQUENCE: 9
atggactgga cttggattct gttcctggtc gctgccgcaa cccgcgtgca ttctggctgg      60
gacctgactg tgaagatgct ggctggaaac gagttccagg tgtctctgag ctcctctatg     120
tctgtgagcg agctgaaggc ccagatcacc cagaagatcg gcgtgcacgc ctttcagcag     180
aggctggccg tgcaccctag cggcgtggcc ctgcaggacc gcgtgccact ggcatcccag     240
ggactgggac caggctctac cgtgctgctg gtggtggaca agtgcgatga ccactgagc      300 atcctggtgc ggaacaataa gggcagaagc tccacatacg aggtgcggct gacccagaca     360
gtggcccacc tgaagcagca ggtgtccgga ctggaggggag tgcaggacga tctgttctgg     420
ctgacatttg agggcaagcc cctggaggat cagctgcctc tgggcgagta tggcctgaag     480
cccctgtcaa ccgtgtttat gaatctggct ctggcagcag caggcaccga accaggcggg     540
aggagc                                                               546

<210> SEQ ID NO 10
<211> LENGTH: 182
<212> TYPE: PRT
<213> ORGANISM: Artificial Sequence
<220> FEATURE:
<223> OTHER INFORMATION: mut ISG15 human vers.2 protein

<400> SEQUENCE: 10

```
Met Asp Trp Thr Trp Ile Leu Phe Leu Val Ala Ala Thr Arg Val
1               5                   10                  15

His Ser Gly Trp Asp Leu Thr Val Lys Met Leu Ala Gly Asn Glu Phe
            20                  25                  30

Gln Val Ser Leu Ser Ser Ser Met Ser Val Ser Glu Leu Lys Ala Gln
        35                  40                  45

Ile Thr Gln Lys Ile Gly Val His Ala Phe Gln Gln Arg Leu Ala Val
    50                  55                  60

His Pro Ser Gly Val Ala Leu Gln Asp Arg Val Pro Leu Ala Ser Gln
65                  70                  75                  80

Gly Leu Gly Pro Gly Ser Thr Val Leu Leu Val Val Asp Lys Cys Asp
                85                  90                  95

Glu Pro Leu Ser Ile Leu Val Arg Asn Asn Lys Gly Arg Ser Ser Thr
            100                 105                 110

Tyr Glu Val Arg Leu Thr Gln Thr Val Ala His Leu Lys Gln Gln Val
        115                 120                 125

Ser Gly Leu Glu Gly Val Gln Asp Asp Leu Phe Trp Leu Thr Phe Glu
    130                 135                 140

Gly Lys Pro Leu Glu Asp Gln Leu Pro Leu Gly Glu Tyr Gly Leu Lys
145                 150                 155                 160

Pro Leu Ser Thr Val Phe Met Asn Leu Ala Leu Ala Ala Ala Gly Thr
                165                 170                 175

Glu Pro Gly Gly Arg Ser
            180
```

<210> SEQ ID NO 11
<211> LENGTH: 9
<212> TYPE: PRT
<213> ORGANISM: Artificial Sequence
<220> FEATURE:
<223> OTHER INFORMATION: CD8 HPV16 E7 epitope

<400> SEQUENCE: 11

```
Arg Ala His Tyr Asn Ile Val Thr Phe
1               5
```

<210> SEQ ID NO 12
<211> LENGTH: 6
<212> TYPE: PRT
<213> ORGANISM: Artificial Sequence
<220> FEATURE:
<223> OTHER INFORMATION: C-terminal conjugation site for ISG15

<400> SEQUENCE: 12

```
Leu Arg Leu Arg Gly Gly
1               5
```

<210> SEQ ID NO 13
<211> LENGTH: 6
<212> TYPE: PRT
<213> ORGANISM: Artificial Sequence
<220> FEATURE:
<223> OTHER INFORMATION: mutated C-terminal site for ISG15

```
<400> SEQUENCE: 13

Ala Ala Ala Ala Gly Gly
1               5
```

ISG15 AND ITS USE AS AN ADJUVANT

CROSS-REFERENCE TO RELATED APPLICATIONS

This application is the U.S. national stage application filed under 35 U.S.C. § 371 claiming benefit to International Patent Application No. PCT/US2016/023306, filed Mar. 18, 2016, which claims priority to U.S. Provisional Application No. 62/136,325, filed Mar. 20, 2015, which are hereby incorporated by reference in their entirety.

TECHNICAL FIELD

The present invention relates to vaccines comprising an antigen and ISG15, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Interferon-stimulating gene 15 (ISG15) is one of the first and most abundant proteins induced by type I interferon stimulation. ISG15 is an ubiquitin-like protein, which plays a major role in antiviral defense. Its ubiquitin-like C-terminal (LRLRGG) motif is necessary for its conjugation to a variety of intracellular proteins in a process known as ISGylation producing "conjugated" ISG15. When not in this conjugated form, free or "unconjugated" ISG15 can exist intracellularly or extracellularly. For decades, free ISG15 has been implicated in the production of IFNγ. Recently, a new study confirmed this cytokine-like role for ISG15 by demonstrating that ISG15-deficiency was associated with a loss of IFNγ, which in turn led to increased susceptibility to mycobacterial disease in both mice and humans. Although these studies have established the ability of ISG15 to function as an immunomodulatory molecule, its ability to influence CD8 T cell immune responses and act as a vaccine adjuvant remains unknown.

Vaccines are also administered in many different ways (e.g., injection, orally, etc.) into many different tissues (e.g., intramuscular, nasal, etc.). Not all delivery methods, however, are equal. Some delivery methods allow for greater compliance within a population of individuals while other delivery methods may affect immunogenicity and/or safety of the vaccine. Accordingly, a need remains in the art for the development of safe and more effective adjuvants that increase immune responses to the antigen.

SUMMARY OF THE INVENTION

The present invention is directed to a vaccine comprising an antigen and ISG15. ISG15 can be encoded by a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, a nucleotide sequence as set forth in SEQ ID NO:3, a nucleotide sequence having at least about 95% identity to a nucleotide sequence as set forth in SEQ ID NO:5, a nucleotide sequence as set forth in SEQ ID NO:5, a nucleotide sequence having at least about 95% identity to a nucleotide sequence as set forth in SEQ ID NO:7, a nucleotide sequence as set forth in SEQ ID NO:7, a nucleotide sequence having at least about 95% identity to a nucleotide sequence as set forth in SEQ ID NO:9, and a nucleotide sequence as set forth in SEQ ID NO:9. ISG15 can be encoded by the nucleotide sequence as set forth in SEQ ID NO:1. ISG15 can be encoded by the nucleotide sequence as set forth in SEQ ID NO:3. ISG15 can be encoded by the nucleotide sequence as set forth in SEQ ID NO:5. ISG15 can be encoded by the nucleotide sequence as set forth in SEQ ID NO:7. ISG15 can be encoded by the nucleotide sequence as set forth in SEQ ID NO:9.

The antigen can be encoded by a first nucleic acid and ISG15 can be encoded by a second nucleic acid. The second nucleic acid can further comprise an expression vector. The first nucleic acid may further comprise an expression vector. The vaccine may further comprise an antigen peptide encoded by one of SEQ ID NO:1, SEQ ID NO:3, SEQ ID NO:5, SEQ ID NO:7, or SEQ ID NO:9. The vaccine may further comprise an ISG15 peptide encoded by one of SEQ ID NO:2, SEQ ID NO:4, SEQ ID NO:6, SEQ ID NO:8, or SEQ ID NO:10. The vaccine may further comprise an antigen peptide encoded by one of SEQ ID NO:1, SEQ ID NO:3, SEQ ID NO:5, SEQ ID NO:7, or SEQ ID NO:9, and an ISG15 peptide encoded by one of SEQ ID NO:2, SEQ ID NO:4, SEQ ID NO:6, SEQ ID NO:8, or SEQ ID NO:10.

The antigen can be selected from the group consisting of: a human papilloma virus (HPV) antigen, an Human Immunodeficiency Virus (HIV) antigen, an influenza antigen, a *Plasmodium falciparum* antigen, a *Mycobacterium tuberculosis* antigen, a lymphocytic choriomeningitis (LCMV) antigen, and a fragment thereof. The HPV antigen can be selected from the group consisting of: HPV16 E6 antigen, HPV16 E7 antigen, and a combination thereof. The HIV antigen can be selected from the group consisting of: Env A, Env B, Env C, Env D, B Nef-Rev, Gag, and any combination thereof. The influenza antigen can be selected from the group consisting of: H1 HA, H2 HA, H3 HA, H5 HA, BHA antigen, and any combination thereof. The *Plasmodium falciparum* antigen can include a circumsporozoite (CS) antigen. The *Mycobacterium tuberculosis* antigen can be selected from the group consisting of: Ag85A, Ag85B, EsxA, EsxB, EsxC, EsxD, EsxE, EsxF, EsxH, EsxO, EsxQ, EsxR, EsxS, EsxT, EsxU, EsxV, EsxW, and any combination thereof. The LCMV antigen can be selected from the group consisting of: nucleoprotein (NP), glycoprotein (GP), and a combination thereof.

The vaccine can further comprise a pharmaceutically acceptable excipient.

The present invention is also directed to a method for increasing or inducing an immune response in a subject in need thereof. The method can comprise administering a vaccine comprising an antigen and ISG15 to the subject. ISG15 can be encoded by a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, a nucleotide sequence as set forth in SEQ ID NO:3, a nucleotide sequence having at least about 95% identity to a nucleotide sequence as set forth in SEQ ID NO:5, a nucleotide sequence as set forth in SEQ ID NO:5, a nucleotide sequence having at least about 95% identity to a nucleotide sequence as set forth in SEQ ID NO:7, a nucleotide sequence as set forth in SEQ ID NO:7, a nucleotide sequence having at least about 95% identity to a nucleotide sequence as set forth in SEQ ID NO:9, and a nucleotide sequence as set forth in SEQ ID NO:9. ISG15 can be encoded by the nucleotide sequence as set forth in SEQ ID NO:1. ISG15 can be encoded by the nucleotide sequence as set forth in SEQ ID NO:3. ISG15 can be encoded by the nucleotide sequence as set forth in SEQ ID NO:5. ISG15 can be encoded by the nucleotide sequence as set forth in SEQ ID NO:7. ISG15 can be encoded by the nucleotide sequence as set forth in SEQ ID NO:9.

Administering the vaccine can include electroporation. The immune response in the subject can be increased by at least about 2-fold. The immune response in the subject can be increased by at least about 4-fold. Increasing the immune response in the subject can include increasing a cellular immune response in the subject.

The present invention is further directed to a method for treating cancer in a subject in need thereof. The method can comprise administering a vaccine comprising an antigen and ISG15 to the subject. ISG15 can be encoded by a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, a nucleotide sequence as set forth in SEQ ID NO:3, a nucleotide sequence having at least about 95% identity to a nucleotide sequence as set forth in SEQ ID NO:5, a nucleotide sequence as set forth in SEQ ID NO:5, a nucleotide sequence having at least about 95% identity to a nucleotide sequence as set forth in SEQ ID NO:7, a nucleotide sequence as set forth in SEQ ID NO:7, a nucleotide sequence having at least about 95% identity to a nucleotide sequence as set forth in SEQ ID NO:9, and a nucleotide sequence as set forth in SEQ ID NO:9. ISG15 can be encoded by the nucleotide sequence as set forth in SEQ ID NO:1. ISG15 can be encoded by the nucleotide sequence as set forth in SEQ ID NO:3. ISG15 can be encoded by the nucleotide sequence as set forth in SEQ ID NO:5. ISG15 can be encoded by the nucleotide sequence as set forth in SEQ ID NO:7. ISG15 can be encoded by the nucleotide sequence as set forth in SEQ ID NO:9.

The method for treating cancer can further comprise reducing tumor size in the subject. The tumor size may be reduced by at least 10% in the subject, as compared to administering a vaccine without ISG15. The method for treating cancer can further comprise increasing tumor regression in the subject. The tumor regression may be increased by at least 10% in the subject, compared to administering a vaccine without ISG15. The cancer can be selected from the group consisting of: an HPV-associated cancer, an HBV-associated cancer, an ovarian cancer, a prostate cancer, a breast cancer, a brain cancer, a head and neck cancer, a throat cancer, a lung cancer, a liver cancer, a cancer of the pancreas, a kidney cancer, a bone cancer, a melanoma, a metastatic cancer, an hTERT-associated cancer, a FAP-antigen associated cancer, a non-small cell lung cancer, a blood cancer, an esophageal squamous cell carcinoma, a cervical cancer, a bladder cancer, a colorectal cancer, a gastric cancer, an anal cancer, a synovial carcinoma, a testicular cancer, a recurrent respiratory papillomatosis, a skin cancer, a glioblastoma, a hepatocarcinoma, a stomach cancer, an acute myeloid leukemia, a triple-negative breast cancer, and primary cutaneous T cell lymphoma. The cancer can be the HPV-associated cancer.

The present invention is further directed to a nucleic acid molecule comprising one or more nucleotide sequences selected from the group consisting of: SEQ ID NO:1, SEQ ID NO:3, SEQ ID NO:5, SEQ ID NO:7, SEQ ID NO:9, a nucleotide sequence that is 95% identical or greater to SEQ ID NO:1, a nucleotide sequence that is 95% identical or greater to SEQ ID NO:3, a nucleotide sequence that is 95% identical or greater to SEQ ID NO:5, a nucleotide sequence that is 95% identical or greater to SEQ ID NO:7, a nucleotide sequence that is 95% identical or greater to SEQ ID NO:9, and any combination thereof. The nucleic acid molecule can be a plasmid. The nucleic acid molecule can be one or more plasmids.

DETAILED DESCRIPTION

Figure 1:
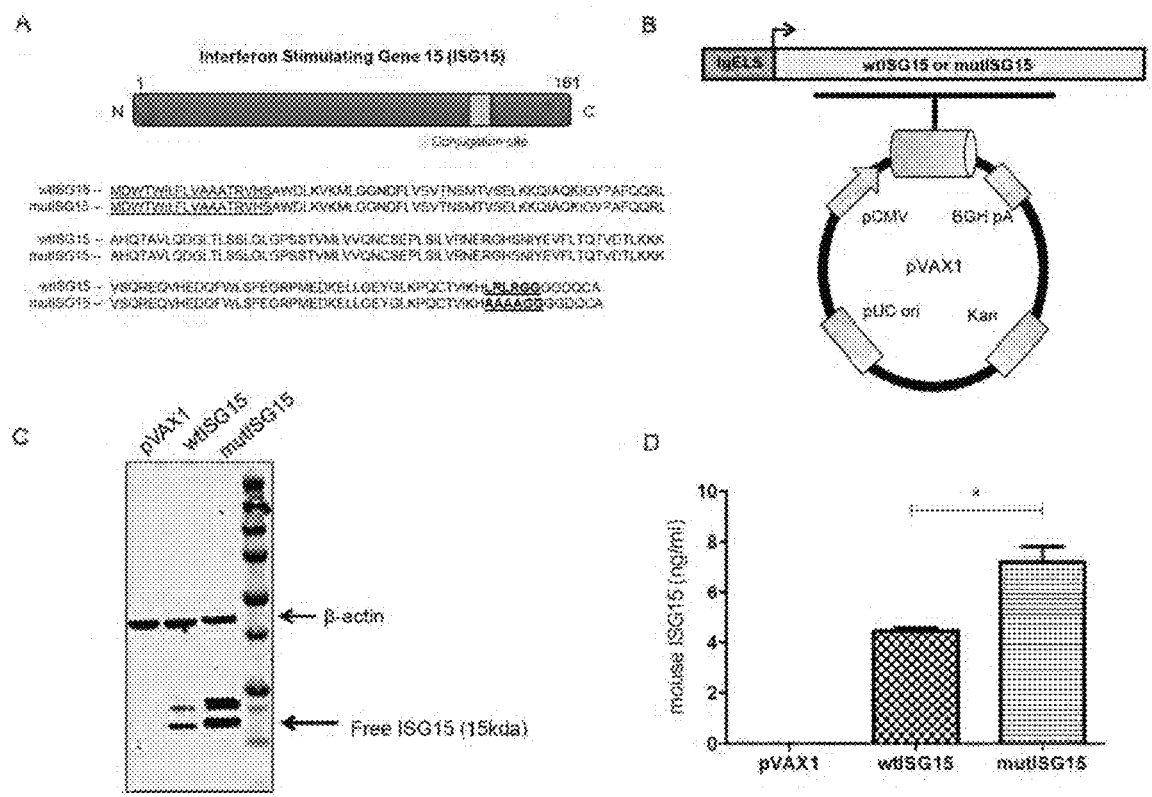
FIG. 1. Generation and expression of ISG15 encoding DNA vaccine plasmids. (A) Schematic illustration of ISG15 protein and the amino acid sequences of wild-type ISG15 (wtISG15) and mutated ISG15 (mutISG15). The IgE leader sequences are underlined. The C-terminal ubiquitin-like conjugation site is bold and underlined. The mutation sites introduced into the conjugation motif for mutISG15 (unconjugated form) are in red. (B) map of ISG15 constructs. (C) Expression of ISG15 constructs examined by Western blot analysis. The lowest band represents free ISG15. (D) Detection of secreted wtISG15 and mutISG15 from transfected RD cells were confirmed via ELISA. Data represents the means with SEM for two replicate assays.

The present invention relates to a vaccine that can be used to increase an immune response to an antigen in a subject by using ISG15 as an adjuvant. When used as an adjuvant, ISG15 can increase the levels of the anti-viral cytokines Interferon-gamma (IFN-γ) and tumor necrosis factor alpha (TNF-α), as well as interleukin-2 (IL-2). Accordingly, ISG15 can increase subpopulations of polyfunctional CD8+ T cells to promote the cellular immune response.

The ISG15 can augment the cellular immune response to antigens such as viral and bacterial antigens, for example, a human papilloma virus (HPV) antigen and a lymphocytic choriomeningitis virus (LCMV) antigen. As such, ISG15 can promote significant protection against such pathogens.

Furthermore, the vaccine of the present invention can prevent cancer or tumor formation. The vaccine can cause regression of established cancers or tumors. For example, the regression can be 90% or greater, as demonstrated by reduction in tumor size. In some instances, the regression of the cancer can be complete. The vaccine can further prevent and cause regression of virus-associated cancers, for example, HPV-associated cancers. Accordingly, also provided herein is a method for the treatment of cancer by administering the vaccine to a subject in need thereof.

The vaccine comprises an antigen and ISG15. ISG15 can be encoded by a nucleotide sequence selected from the group consisting of: a nucleotide sequence encoding a protein sequence having: at least about 95% identity to a nucleotide sequence as set forth in SEQ ID NO:1, at least about 96% identity to a nucleotide sequence as set forth in SEQ ID NO:1, at least about 97% identity to a nucleotide sequence as set forth in SEQ ID NO:1, at least about 98% identity to a nucleotide sequence as set forth in SEQ ID NO:1, at least about 99% identity to a nucleotide sequence as set forth in SEQ ID NO:1, and a nucleotide sequence as set forth in SEQ ID NO:1.

ISG15 can be encoded by a nucleotide sequence selected from the group consisting of: a nucleotide sequence encoding a protein sequence having: at least about 95% identity to a nucleotide sequence as set forth in SEQ ID NO:3, at least about 96% identity to a nucleotide sequence as set forth in SEQ ID NO:3, at least about 97% identity to a nucleotide sequence as set forth in SEQ ID NO:3, at least about 98% identity to a nucleotide sequence as set forth in SEQ ID NO:3, at least about 99% identity to a nucleotide sequence as set forth in SEQ ID NO:3, and a nucleotide sequence as set forth in SEQ ID NO:3.

ISG15 can be encoded by a nucleotide sequence selected from the group consisting of: a nucleotide sequence encoding a protein sequence having: at least about 95% identity to a nucleotide sequence as set forth in SEQ ID NO:5, at least about 96% identity to a nucleotide sequence as set forth in SEQ ID NO:5, at least about 97% identity to a nucleotide sequence as set forth in SEQ ID NO:5, at least about 98% identity to a nucleotide sequence as set forth in SEQ ID NO:5, at least about 99% identity to a nucleotide sequence as set forth in SEQ ID NO:5 and a nucleotide sequence as set forth in SEQ ID NO:5.

ISG15 can be encoded by a nucleotide sequence selected from the group consisting of: a nucleotide sequence encoding a protein sequence having: at least about 95% identity to a nucleotide sequence as set forth in SEQ ID NO:7, at least about 96% identity to a nucleotide sequence as set forth in SEQ ID NO:7, at least about 97% identity to a nucleotide sequence as set forth in SEQ ID NO:7, at least about 98% identity to a nucleotide sequence as set forth in SEQ ID NO:7, at least about 99% identity to a nucleotide sequence as set forth in SEQ ID NO:1, and a nucleotide sequence as set forth in SEQ ID NO:7.

ISG15 can be encoded by a nucleotide sequence selected from the group consisting of: a nucleotide sequence encoding a protein sequence having: at least about 95% identity to a nucleotide sequence as set forth in SEQ ID NO:9, at least about 96% identity to a nucleotide sequence as set forth in SEQ ID NO:9, at least about 97% identity to a nucleotide sequence as set forth in SEQ ID NO:9, at least about 98% identity to a nucleotide sequence as set forth in SEQ ID NO:9, at least about 99% identity to a nucleotide sequence as set forth in SEQ ID NO:9, and a nucleotide sequence as set forth in SEQ ID NO:9.

The ISG15 can augment the cellular immune response to antigens such as viral and bacterial antigens, for example, a human papilloma virus (HPV) antigen, a human immunodeficiency virus (HIV) antigen, a *Mycobacterium tuberculosis* antigen, and a lymphocytic choriomeningitis virus (LCMV) antigen. As such, ISG15 can promote significant protection against such pathogens.

The vaccine of the present invention can prevent cancer or tumor formation. The vaccine can also cause regression of established cancer or tumors. The regression can be 90% or greater regression. The regression of the cancer can be complete. The vaccine can further prevent and cause regression of virus-associated cancers, for example, HPV-associated cancer. Accordingly, also provided herein is a method for the treatment of cancer by administering the vaccine to a subject in need thereof.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccine described herein to enhance the immunogenicity of the antigens.

"Fragment" as used herein means a nucleic acid sequence or a portion thereof, that encodes a polypeptide capable of eliciting an immune response in a mammal. The fragments can be DNA fragments selected from at least one of the various nucleotide sequences that encode protein fragments set forth below.

"Immune response" as used herein means the activation of a host's immune system, e.g., that of a mammal, in response to the introduction of antigen. The immune response can be in the form of a cellular or humoral response, or both.

"Nucleic acids" as used herein can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Treatment" or "treating," as used herein can mean protection of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease, but before its clinical appearance. Repressing the disease involves administering a vaccine of the present invention to an animal after clinical appearance of the disease.

"Subject" as used herein can mean a mammal that wants to or is in need of being immunized with the herein described vaccine. The mammal can be a human, chimpanzee, dog, cat, horse, cow, mouse, or rat.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly, the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof "Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Vaccine

Provided herein is a vaccine comprising an antigen and an adjuvant. The vaccine can increase antigen presentation and the overall immune response to the antigen in a subject. The combination of antigen and adjuvant induces the immune system more efficiently than a vaccine comprising the antigen alone. The vaccine can further induce an immune response when administered to different tissues such as the muscle and the skin. This more efficient immune response provides increased efficacy in the treatment and/or prevention of any disease, pathogen, or virus, including cancer as described in more detail below.

The vaccine can induce IFN-γ production by at least about 1.5-fold, at least about 2-fold, at least about 3-fold, at least about 4-fold, at least about 5-fold, at least about 8-fold, and at least about 10-fold as compared to a vaccine not including the adjuvant.

The vaccine can increase or boost the cellular and/or humoral immune response to the antigen in a subject as compared to a vaccine without the adjuvant. The vaccine can increase the cellular immune response to the antigen by about 75% to about 200% as compared to a vaccine without the adjuvant. Alternatively, the vaccine can increase the cellular immune response to the antigen by about 90% to about 130% as compared to a vaccine without the adjuvant. The vaccine can increase the cellular immune response to the antigen by about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, about 126%, about 127%, about 128%, about 129%, about 130%, about 131%, about 132%, about 133%, about 134%, about 135%, about 136%, about 137%, about 138%, about 139%, about 140%, about 141%, about 142%, about 143%, about 144%, about 145%, about 146%, about 147%, about 148%, about 149%, about 150%, about 151%, about 152%, about 153%, about 154%, about 155%, about 156%, about 157%, about 158%, about 159%, about 160%, about 161%, about 162%, about 163%, about 164%, about 165%, about 166%, about 167%, about 168%, about 169%, about 170%, about 171%, about 172%, about 173%, about 174%, about 175%, about 176%, about 177%, about 178%, about 179%, about 180%, about 181%, about 182%, about 183%, about 184%, about 185%, about 186%, about 187%, about 188%, about 189%, about 190%, about 191%, about 192%, about 193%, about 194%, about 195%, about 196%, about 197%, about 198%, about 199%, or about 200% as compared to a vaccine without the adjuvant.

The vaccine of the present invention can have features required of effective vaccines such as being safe so that the vaccine itself does not cause illness or death; being protective against illness resulting from exposure to live pathogens such as viruses or bacteria; inducing neutralizing antibody to prevent infection of cells; inducing protective T cell response against intracellular pathogens; and providing ease of administration, few side effects, biological stability, and low cost per dose. The vaccine can accomplish some or all of these features by combining the antigen with the adjuvant as discussed below.

The vaccine can further modify epitope presentation within the antigen to induce greater immune response to the antigen than a vaccine comprising the antigen alone. The vaccine can further induce an immune response when administered to different tissues such as the muscle or the skin.

a. Adjuvant

The vaccine can comprise an adjuvant. The adjuvant can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) ISG15

The adjuvant can be interferon-stimulating gene 15 (ISG15), fragments thereof, variants thereof, or combinations thereof. The ISG15 may be in a conjugated, or conjugatable, form. The ISG15 may be in an unconjugated, or non-conjugatable, form. For example, the conjugated form of ISG15 may have an amino acid sequence as shown in SEQ ID NO:4 or SEQ ID NO:8. The unconjugated form of ISG15 may have an amino acid sequence as shown in SEQ ID NO:2, SEQ ID NO:6, or SEQ ID NO:10, for example.

ISG15 is an ubiquitin-like protein induced by type I interferon and is associated with infectious diseases (i.e., bacterial and viral infections), as well as being an immunomodulatory molecule, wherein ISG15 has been shown to mediate protection against influenza, HIV, and Sindbis virus infection among others.

ISG15 expression is upregulated after cell stress, especially those induced by bacterial and viral infections. These stresses activate transcription factors in IFN signaling, mainly Interferon Regulatory Factor 3 (IRF3) and Interferon-stimulated gene factor 3 (ISGF3), which in turn upregulate expression of ISG15, wherein the promoter of ISG15 contains 2 IFN-stimulated response elements (ISREs). Both external insults (gamma irradiation, anticancer drugs, or viral infection) and internal insults (diseases and aging) can trigger ISG15 expression. It has been shown that ISG15 has a cytokine-like role and its deficiency has been associated with a loss of IFNγ, which in turn led to increased susceptibility to mycobacterial disease in both mice and humans. In addition, recombinant human ISG15 was found to activate leukocytes in vitro when added to culture media and induce production of proinflammatory cytokines.

ISG15 contains 2 ubiquitin-like domains, making it a linear dimer of a ubiquitin-like protein. Type I Interferon produced during an infection induces expression of ISG15, leading to its secretion and, like ubiquitin, conjugation to intracellular substrates through the action of a unique enzymatic cascade. As briefly described above, ISG15 may have an ubiquitin-like C-terminal (LRLRGG (SEQ ID NO:12)) motif that facilitates its conjugation to a variety of intracellular proteins in a process known as ISGylation producing "conjugated" ISG15. When not in this conjugated form, free or "unconjugated" ISG15 can exist intracellularly or extracellularly.

ISG15 can increase or boost the immune response to the antigen in the subject when administered together. The antigen is discussed in more detail below. ISG15 can increase the immune response to the antigen by about 75% to about 200%, compared to administering the antigen without ISG15. In some instances, ISG15 can increase the immune response to the antigen by about 90% to about 150%, compared to administering the antigen without ISG15. In some instances, ISG15 can increase the immune response about 100% to about 130%, compared to administering the vaccine without ISG15. In still other alternative embodiments, ISG15 can increase the immune response to the antigen by about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, about 126%, about 127%, about 128%, about 129%, or about 130%, compared to administering the antigen without ISG15.

In other embodiments, ISG15 can increase or boost the immune response to the antigen by at least 1.5-fold, at least 2.0-fold, at least 2.5-fold, at least 3.0-fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, or at least 10.0-fold, compared to administering the antigen without ISG15.

ISG15 as an adjuvant can increase or boost the Th1 or cellular immune response to the antigen in the subject. The Th1 immune response involves the activation of T cell responses. These T cell responses may include $CD4^+$ and $CD8^+$ T cell responses and the secretion of interferon-gamma, tumor necrosis factor alpha, and/or interleukin (IL-2). Interferon-gamma and tumor necrosis factor alpha have antiviral, immunoregulatory, and anti-tumor properties and can alter transcription in multiple genes to produce a variety of physiological and cellular responses. Some effects by interferon-gamma include promoting natural killer cell (NK cells) activity, causing normal cells to increase expression of class I MHC molecules, increasing antigen presentation and lysosome activity in macrophages, inducing nitric oxide synthase (iNOS), and promoting Th1 differentiation in cellular immunity with regards to cytotoxic $CD8^+$ T cells while suppressing Th2 differentiation in humoral (antibody) immunity.

Cytotoxic $CD8^+$ T cells (cytotoxic T lymphocytes (CTLs)) are a subgroup of T cells that induce the death of cells infected with viruses and other pathogens. Upon activation, CTLs undergo clonal expansion to produce effector cells that are antigen-specific. Effector CTLs release through a process of directed exocytosis (i.e., degranulation) molecules that kill infected or target cells, for example, perforin, granulysin, and granzyme. When no longer needed, many effector CTLs die, but some effector cells are retained as memory cells such that when the antigen is encountered again, the memory cells differentiate into effector cells to more quickly mount an immune response.

When ISG15 increases or boosts the Th1 or cellular immune response, Interferon-gamma (IFN-γ) levels (secretion) are increased. In some instances, ISG15 can increase the Th1 or cellular immune response to the antigen by about 1.5-fold to about 10.0-fold, about 1.5-fold to about 8.0-fold, about 1.5-fold to about 6.0-fold, about 1.5-fold to about 4.0-fold, about 2.0-fold to about 10.0-fold, about 2.0-fold to about 8.0-fold, about 2.0-fold to about 6.0-fold, about 2.0-fold to about 4.0-fold, about 2.5-fold to about 4.0-fold, about 4.0-fold to about 10.0-fold, about 6.0-fold to about 10.0-fold, or about 8.0-fold to about 10.0-fold, compared to administering the antigen without ISG15. ISG15 can also increase the Th1 or cellular immune response to the antigen by at least 2.5-fold, at least 2.6-fold, at least 2.7-fold, at least 2.8-fold, at least 2.9-fold, at least 3.0-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4.0-fold, at least 4.1-fold, at least 4.2-fold, at least 4.3-fold, at least 4.4-fold, at least 4.5-fold, at least 4.6-fold, at least 4.7-fold, at least 4.8-fold, at least 4.9-fold, at least 5.0-fold, at least 6.0-fold, at least 7.0-fold, at least 8.0-fold, at least 9.0-fold, or at least 10.0-fold, compared to administering the antigen without ISG15. ISG15 can further increase the Th1 or cellular immune response by about 2.0-fold, about 2.5-fold, about 3.0-fold, about 3.5-fold, about 4.0-fold, or about 4.5-fold, compared to administering the antigen without ISG15.

The increased or boosted immune response to the antigen can further include an increased CD8$^+$ T cell response. The increased CD8$^+$ T cell response can include increasing in the subject the population or frequency of CD8$^+$ T cells that secrete IFN-$\gamma$, TNF-$\alpha$, or both IFN-$\gamma$ and TNF-$\alpha$, or a combination of IFN-$\gamma$, TNF-$\alpha$, and IL-2 (e.g., triple-positive cells expressing IFN-$\gamma$, TNF-$\alpha$, and IL-2). Accordingly, the increased CD8$^+$ T cell response can include increasing subpopulations of polyfunctional CD8+ T cells.

The increased CD8$^+$ T cell response can also include an increased cytotoxic CD8+T lymphocyte (CTL) response. The increased CTL response can include increasing in the subject the population or frequency of CD8$^+$ T cells undergoing degranulation. The increased CTL response can further include increasing in the subject the population or frequency of CD8+ T cells expressing CD107a. The increased CTL response can further include increasing in the subject the population or frequency of CD8$^+$ T cells co-expressing CD107a and IFN-$\gamma$, or CD107a, IFN-$\gamma$, and TNF-$\alpha$.

The increased or boosted immune response to the antigen can further include the expansion and differentiation of CD8$^+$ T cells in the subject. Such expansion can occur in the periphery. Additionally, recall of established memory CD8$^+$ T cells is increased in the subject. As such, ISG15 can increase the cellular immune response by expanding both effector and effector-memory CD8$^+$ T cell populations that are specific to the antigen. The expanded effector and effector-memory CD8$^+$ T cell populations can have an increased frequency of cells that express KLRG1.

The increased or boosted immune response to the antigen (provided by ISG15) can further include protection against disease associated with the antigen. In some embodiments, the increased or boosted immune response to the antigen can include complete protection against disease associated with the antigen. In some instances, the increased or boosted immune response to the antigen can include about 70% to about 100%, about 75% to about 95% survival, or about 75% to about 85% survival rate against disease associated with the antigen, compared to survival rate against disease with the antigen when ISG15 is not an adjuvant. In other embodiments, the increased or boosted immune response to the antigen can include at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least or 100% survival rate against disease associated with the antigen, compared to survival rate against disease with the antigen when ISG15 is not an adjuvant.

A nucleic acid encoding ISG15 can be from any number of organisms, for example, mouse (*Mus musculus*), macaque (*Macacac mulatta*), and human (*Homo sapiens*). In a preferred embodiment, the nucleic acid encoding ISG15 is a human ISG15 nucleic acid. For example, the human ISG15 nucleic acid may be SEQ ID NO:5, SEQ ID NO:7, or SEQ ID NO:9. In another embodiment, the nucleic acid encoding ISG15 is a mouse ISG15 nucleic acid. For example, the mouse ISG15 nucleic acid may be SEQ ID NO: 1 or SEQ ID NO:3. The nucleic acid encoding ISG15 can be optimized with regards to codon usage and corresponding RNA transcripts. The nucleic acid encoding ISG15 can be codon and RNA optimized for expression. In some embodiments, the nucleic acid encoding ISG15 can include a Kozak sequence (e.g., GCC ACC) to increase the efficiency of translation. The nucleic acid encoding ISG15 can include multiple stop codons (e.g., TGA TGA) to increase the efficiency of translation termination. The nucleic acid encoding ISG15 can also include a nucleotide sequence encoding an IgE leader sequence. The IgE leader sequence can be located 5' to the ISG15 in the nucleic acid. In some embodiments, the nucleic acid encoding ISG15 is free of or does not contain a nucleotide sequence encoding the IgE leader sequence.

ISG15 can be the optimized nucleic acid sequence SEQ ID NO:1, which encodes for SEQ ID NO:2. In some embodiments, ISG15 can be the nucleic acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the nucleic acid sequence set forth in SEQ ID NO:1. In other embodiments, ISG15 can be the nucleic acid sequence that encodes the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. identity over an entire length of the amino acid sequence set forth in SEQ ID NO:2. ISG15 can be the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the amino acid sequence set forth in SEQ ID NO:2.

Some embodiments relate to fragments of SEQ ID NO:1. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:1 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1. Some embodiments relate to fragments that have 96% or greater identity to the fragments of ISG15 nucleic acid sequences herein. Some embodiments relate to fragments that have 97% or greater identity to the fragments of ISG15 nucleic acid sequences herein. Some embodiments relate to fragments that have 98% or greater identity to the fragments of ISG15 nucleic acid sequences herein. Some embodiments relate to fragments that have 99% or greater identity to the fragments of ISG15 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:2 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:2 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2. Some embodiments relate to fragments having 96% or greater identity to the fragments of ISG15 protein sequences herein. Some embodiments relate to fragments having 97% or greater identity to the fragments of ISG15 protein sequences herein. Some embodiments relate to fragments having 98% or greater identity to the fragments of ISG15 protein sequences herein. Some embodiments relate to fragments having 99% or greater identity to the fragments of ISG15 protein sequences herein. In some embodiments, fragments include a leader sequence, for example, an immunoglobulin leader sequence such as the IgE leader sequence. In some embodiments, the fragments are free of a leader sequence.

ISG15 can be the optimized nucleic acid sequence SEQ ID NO:3, which encodes for SEQ ID NO:4. In some embodiments, ISG15 can be the nucleic acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the nucleic acid sequence set forth in SEQ ID NO:3. In other embodiments, ISG15 can be the nucleic acid sequence that encodes the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. identity over an entire length of the amino acid sequence set forth in SEQ ID NO:4. ISG15 can be the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the amino acid sequence set forth in SEQ ID NO:4.

Some embodiments relate to fragments of SEQ ID NO:3. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:3. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:3 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:3. Some embodiments relate to fragments that have 96% or greater identity to the fragments of ISG15 nucleic acid sequences herein. Some embodiments relate to fragments that have 97% or greater identity to the fragments of ISG15 nucleic acid sequences herein. Some embodiments relate to fragments that have 98% or greater identity to the fragments of ISG15 nucleic acid sequences herein. Some embodiments relate to fragments that have 99% or greater identity to the fragments of ISG15 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:4 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:4. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:4 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:4. Some embodiments relate to fragments having 96% or greater identity to the fragments of ISG15 protein sequences herein. Some embodiments relate to fragments having 97% or greater identity to the fragments of ISG15 protein sequences herein. Some embodiments relate to fragments having 98% or greater identity to the fragments of ISG15 protein sequences herein. Some embodiments relate to fragments having 99% or greater identity to the fragments of ISG15 protein sequences herein. In some embodiments, fragments include a leader sequence, for example, an immunoglobulin leader sequence such as the IgE leader sequence. In some embodiments, the fragments are free of a leader sequence.

ISG15 can be the optimized nucleic acid sequence SEQ ID NO:5, which encodes for SEQ ID NO:6. In some embodiments, ISG15 can be the nucleic acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the nucleic acid sequence set forth in SEQ ID NO:5. In other embodiments, ISG15 can be the nucleic acid sequence that encodes the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. identity over an entire length of the amino acid sequence set forth in SEQ ID NO:6. ISG15 can be the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the amino acid sequence set forth in SEQ ID NO:6.

Some embodiments relate to fragments of SEQ ID NO:5. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:5. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:5 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:5. Some embodiments relate to fragments that have 96% or greater identity to the fragments of ISG15 nucleic acid sequences herein. Some embodiments relate to fragments that have 97% or greater identity to the fragments of ISG15 nucleic acid sequences herein. Some embodiments relate to fragments that have 98% or greater identity to the fragments of ISG15 nucleic acid sequences herein. Some embodiments relate to fragments that have 99% or greater identity to the fragments of ISG15 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:6 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:6. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:6 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:6. Some embodiments relate to fragments having 96% or greater identity to the fragments of ISG15 protein sequences herein. Some embodiments relate to fragments having 97% or greater identity to the fragments of ISG15 protein sequences herein. Some embodiments relate to fragments having 98% or greater identity to the fragments of ISG15 protein sequences herein. Some embodiments relate to fragments having 99% or greater identity to the fragments of ISG15 protein sequences herein. In some embodiments, fragments include a leader sequence, for example, an immunoglobulin leader sequence such as the IgE leader sequence. In some embodiments, the fragments are free of a leader sequence.

ISG15 can be the optimized nucleic acid sequence SEQ ID NO:7, which encodes for SEQ ID NO:8. In some embodiments, ISG15 can be the nucleic acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the nucleic acid sequence set forth in SEQ ID NO:7. In other embodiments, ISG15 can be the nucleic acid sequence that encodes the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 9'7%, about 98%, about 99%, or about 100%. identity over an entire length of the amino acid sequence set forth in SEQ ID NO:8. ISG15 can be the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 9'7%, about 98%, about 99%, or about 100% identity over an entire length of the amino acid sequence set forth in SEQ ID NO:8.

Some embodiments relate to fragments of SEQ ID NO:7. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:7. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:7 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:7. Some embodiments relate to fragments that have 96% or greater identity to the fragments of ISG15 nucleic acid sequences herein. Some embodiments relate to fragments that have 97% or greater identity to the fragments of ISG15 nucleic acid sequences herein. Some embodiments relate to fragments that have 98% or greater identity to the fragments of ISG15 nucleic acid sequences herein. Some embodiments relate to fragments that have 99% or greater identity to the fragments of ISG15 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:8 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:8. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:8 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:8. Some embodiments relate to fragments having 96% or greater identity to the fragments of ISG15 protein sequences herein. Some embodiments relate to fragments having 97% or greater identity to the fragments of ISG15 protein sequences herein. Some embodiments relate to fragments having 98% or greater identity to the fragments of ISG15 protein sequences herein. Some embodiments relate to fragments having 99% or greater identity to the fragments of ISG15 protein sequences herein. In some embodiments, fragments include a leader sequence, for example, an immunoglobulin leader sequence such as the IgE leader sequence. In some embodiments, the fragments are free of a leader sequence.

ISG15 can be the optimized nucleic acid sequence SEQ ID NO:9, which encodes for SEQ ID NO:10. In some embodiments, ISG15 can be the nucleic acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the nucleic acid sequence set forth in SEQ ID NO:9. In other embodiments, ISG15 can be the nucleic acid sequence that encodes the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. identity over an entire length of the amino acid sequence set forth in SEQ ID NO:10. ISG15 can be the amino acid sequence having at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity over an entire length of the amino acid sequence set forth in SEQ ID NO:10.

Some embodiments relate to fragments of SEQ ID NO:9. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:9. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:9 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:9. Some embodiments relate to fragments that have 96% or greater identity to the fragments of ISG15 nucleic acid sequences herein. Some embodiments relate to fragments that have 97% or greater identity to the fragments of ISG15 nucleic acid sequences herein. Some embodiments relate to fragments that have 98% or greater identity to the fragments of ISG15 nucleic acid sequences herein. Some embodiments relate to fragments that have 99% or greater identity to the fragments of ISG15 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:10 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:8. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:10 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:10. Some embodiments relate to fragments having 96% or greater identity to the fragments of ISG15 protein sequences herein. Some embodiments relate to fragments having 97% or greater identity to the fragments of ISG15 protein sequences herein. Some embodiments relate to fragments having 98% or greater identity to the fragments of ISG15 protein sequences herein. Some embodiments relate to fragments having 99% or greater identity to the fragments of ISG15 protein sequences herein. In some embodiments, fragments include a leader sequence, for example, an immunoglobulin leader sequence such as the IgE leader sequence. In some embodiments, the fragments are free of a leader sequence.

b. Antigen

The vaccine can also comprise an antigen or fragment or variant thereof and the adjuvant as discussed above. The antigen can be anything that induces an immune response in a subject. Purified antigens are not usually strongly immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). Preferably, the antigen can be associated with influenza or HIV.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, lymphocytic choriomeningitis virus (LCMV), or cancer causing virus.

(a) Hepatitis Antigen

ISG15 can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a heterologous nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen

ISG15 can be associated or combined with a human papilloma virus (HPV) antigen, or fragment thereof, or variant thereof. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(c) RSV Antigen

ISG15 can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be an optimized amino acid RSV F amino acid sequence, or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be an optimized amino acid RSV G amino acid sequence, or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, the RSV M2-2 protein from the RSV Long strain, the RSV L protein from the RSV Long strain, the RSV G protein from the RSV subtype B isolate H5601, the RSV G protein from the RSV subtype B isolate H1068, the RSV G protein from the RSV subtype B isolate H5598, the RSV G protein from the RSV subtype B isolate H1123, or fragment thereof, or variant thereof.

(d) Influenza Antigen

ISG15 can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen comprising a consensus H1 amino acid sequence or a consensus H2 amino acid sequence. The consensus hemagglutinin antigen may be a synthetic hybrid consensus H1 sequence comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminus an IgE or IgG leader amino acid sequence. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. In some embodiments, consensus hemagglutinin antigen may further comprise on its N-terminus an IgE or IgG leader amino acid sequence and on its C terminus an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an HA Tag at the C-terminus of the protein.

(e) Human Immunodeficiency Virus (HIV) Antigen

ISG15 can be associated or combined with an HIV antigen or fragment thereof, or variant thereof. HIV antigens can include modified consensus sequences for immunogens. Genetic modifications including codon optimization, RNA optimization, and the addition of a high efficient immunoglobin leader sequence to increase the immunogenicity of constructs can be included in the modified consensus sequences. The novel immunogens can be designed to elicit stronger and broader cellular immune responses than corresponding codon optimized immunogens.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments, the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(f) Lymphocytic Choriomeningitis Virus (LCMV) Antigen

ISG15 can be associated or combined with an LCMV antigen or fragment thereof, or variant thereof. The LCMV antigen can comprise consensus sequences and/or one or more modifications for improved expression. Genetic modifications, including codon optimization, RNA optimization, and the addition of a highly efficient immunoglobulin leader sequence to increase the immunogenicity of constructs, can be included in the modified sequences. The LCMV antigen can comprise a signal peptide such as an immunoglobulin signal peptide (e.g., IgE or IgG signal peptide), and in some embodiments, may comprise an HA tag. The immunogens can be designed to elicit stronger and broader cellular immune responses than a corresponding codon optimized immunogen.

The LCMV antigen can be an antigen from LCMV Armstrong. The LCMV antigen can be an antigen from LCMV clone 13. The LCMV antigen can be a nucleoprotein (NP) from LCMV, a glycoprotein (GP; e.g., GP-1, GP-2, and GP-C) from LCMV, a L protein from LCMV, a Z polypeptide from LCMV, a fragment thereof, a variant thereof, or a combination thereof.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa, Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti.*

(a) Malaria Antigen

ISG15 can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS, LSA1, TRAP, CelTOS, and Ama1. The immunogens may be full length or immunogenic fragments of full length proteins. The immunogens comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA tag.

In further embodiments, the malaria antigen can be Ama1, which is a highly conserved *Plasmodium* antigen. The malaria antigen can also be a consensus sequence of Ama1 (i.e., ConAmaI immunogen) comprising in some instances, a signal peptide such as an immunoglobulin signal peptide such as an IgE or IgG signal peptide and in some embodiments, may comprise an HA tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA tag.

In other embodiments, the malaria antigen can be a fusion protein comprising a combination of two or more of the PF proteins set forth herein. For example, fusion proteins may comprise two or more of Consensus CS immunogen, Con- LSA1 immunogen, ConTRAP immunogen, ConCelTOS immunogen and ConAma1 immunogen linked directly adjacent to each other or linked with a spacer or one or more amino acids in between. In some embodiments, the fusion protein comprises two PF immunogens; in some embodiments the fusion protein comprises three PF immunogens; in some embodiments the fusion protein comprises four PF immunogens; and in some embodiments the fusion protein comprises five PF immunogens. Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N terminus. In some embodiments, the fusion proteins comprise multiple signal peptides linked to the N terminus of each Consensus PF immunogen. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein, wherein the spacer is a proteolyic cleavage site recognized by a protease found in cells to which the vaccine is intended to be administered and/or taken up and the fusion protein comprises multiple signal peptides linked to the N terminus of each Consensus PF immunogens such that upon cleavage, the signal peptide of each Consensus PF immunogen translocates the Consensus PF immunogen to outside the cell.

(3) Bacterial Antigens

The antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an *halophile*, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani*, *Yersinia pestis*, *Bacillus anthracis*, methicillin-resistant *Staphylococcus aureus* (MRSA), or *Clostridium difficile*. The bacterium can be *Mycobacterium tuberculosis*.

(a) *Mycobacterium tuberculosis* Antigens

ISG15 can be associated or combined with a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

In some embodiments, the TB antigen can be nucleic acid molecules such as plasmids which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(4) Fungal Antigens

The antigen can be a fungal antigen or fragment or variant thereof. The fungus can be *Aspergillus* species, *Blastomyces dermatitidis*, *Candida* yeasts (e.g., *Candida albicans*), *Coccidioides*, *Cryptococcus neoformans*, *Cryptococcus gattii*, dermatophyte, *Fusarium* species, *Histoplasma capsulatum*, Mucoromycotina, *Pneumocystis jirovecii*, *Sporothrix schenckii*, *Exserohilum*, or *Cladosporium*.

c. Vector

The vaccine can comprise one or more vectors that include a nucleic acid encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, or one or more desired adjuvants. The LEC may be any linear DNA devoid of any phosphate backbone. The DNA may encode one or more antigens, or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The LEC may be derived from any plasmid capable of being linearized. The plasmid may be capable of expressing the antigen, or the adjuvant. The plasmid may be capable of expressing the adjuvant ISG15. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than ISG15, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to ISG15. The additional adjuvant can be other genes that are expressed in an alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, WIC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to ISG15 include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. The vaccine can further comprise stabilizers including gelatin and albumin. The stabilizers can allow the formulation to be stable at room or ambient temperature for extended periods of time, including LGS or polycations or polyanions.

3. Method Of Vaccination

The present invention is also directed to a method of increasing an immune response in a subject. Increasing the immune response can be used to treat and/or prevent disease in the subject, for example, cancer as described in more detail below. The method can include administering the herein disclosed vaccine to the subject. The subject administered the vaccine can have an increased or boosted immune response as compared to a subject administered the antigen alone. In some embodiments, the immune response can be increased by about 75% to about 200%. Alternatively, the immune response in the subject administered the vaccine can be increased by about 90% to about 130%. In still other alternative embodiments, the immune response in the subject administered the vaccine can be increased by about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, about 126%, about 127%, about 128%, about 129%, or about 130%.

In other embodiments, the immune response in the subject administered the vaccine can be increased by at least 1.5-fold, at least 2.0-fold, at least 2.5-fold, at least 3.0-fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, or at least 10.0-fold.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Treatment and Prevention of Cancer

The subject administered the vaccine can have an increased or boosted immune response as compared to the subject administered the antigen alone. The increased immune response can be used to treat and/or prevent disease in the subject. The disease can be cancer, for example, an HPV-associated cancer, HBV-associated cancer, ovarian cancer, prostate cancer, breast cancer, brain cancer, head and neck cancer, throat cancer, lung cancer, liver cancer, cancer of the pancreas, kidney cancer, bone cancer, melanoma, metastatic cancer, hTERT-associated cancer, FAP-antigen associated cancer, non-small cell lung cancer, blood cancer, esophageal squamous cell carcinoma, cervical cancer, bladder cancer, colorectal cancer, gastric cancer, anal cancer, synovial carcinoma, testicular cancer, recurrent respiratory papillomatosis, skin cancer, glioblastoma, hepatocarcinoma, stomach cancer, acute myeloid leukemia, triple-negative breast cancer, and primary cutaneous T cell lymphoma. The cancer can be HPV-associated cancer.

The method can further include reducing the size of an established tumor or lesion in the subject. The tumor can be reduced in size by about 50% to about 100%, about 60% to about 100%, about 70% to about 100%, about 80% to about 100%, about 90% to about 100%, about 50% to about 95%, about 60% to about 95%, about 70% to about 95%, about 80% to about 95%, about 90% to about 95%, about 50% to about 90%, about 60% to about 90%, about 70% to about 90%, or about 80% to about 90%, compared to administering the vaccine without ISG15. The tumor can be reduced in size by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%, compared to administering the vaccine without ISG15.

In some embodiments, administration of the vaccine can tumor can reduce tumor size by at least 10%, by at least 20%, by at least 30%, by at least 40%, by at least 50%, by at least 60%, by at least 70%, by at least 80%, or by at least 90%, compared to administering the vaccine without ISG15.

The method can further include increasing tumor regression in the subject as compared to the subject administered the antigen alone. Administration of the vaccine can increase tumor regression by about 40% to about 60%, about 45% to about 55%, or about 50%, compared to administering the vaccine without ISG15. Administration of the vaccine can also increase the rate of tumor regression. Administration of the vaccine can further achieve tumor regression in the subject of about 80% to about 100%, about 85% to about 100%, about 90% to about 100%, about 95% to about 100%, about 80% to about 95%, about 85% to about 95%, about 90% to about 95%, about 80% to about 90%, or about 85% to about 90%, compared to administering the vaccine without ISG15. Tumor regression can be about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% in the subject administered the vaccine, compared to administering the vaccine without ISG15. Tumor regression in the subject administered the vaccine can further be about 90% or about 100%.

In some embodiments, administration of the vaccine can increase tumor regression by at least 10%, by at least 20%, by at least 30%, by at least 40%, by at least 50%, by at least 60%, by at least 70%, by at least 80%, or by at least 90%, compared to administering the vaccine without ISG15.

The method can further include preventing cancer or tumor growth in the subject administered the vaccine. This prevention can allow the subject administered the vaccine to survive a future cancer. In other words, the vaccine affords protection against cancer to the subject administered the vaccine. The subject administered the vaccine can have about 90% to about 100% survival of cancer, compared to administering the vaccine without ISG15. The subject administered the vaccine can have about 90%, about 91%, about 92%, about 93%, about 94%, about 95%, about 96%, about 97%, about 98%, about 99%, or about 100% survival of cancer, compared to administering the vaccine without ISG15.

b. Treatment and Prevention of Infectious Disease

The subject administered the vaccine can have an increased or boosted immune response as compared to the subject administered the antigen alone. The increased immune response can be used to treat and/or prevent disease in the subject. The disease can be infectious disease, for example, viral and bacterial infections. The bacterial infection can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile*. The bacterium can be *Mycobacterium tuberculosis. listeria monocytogenes*, lymphocytic choriomeningitis virus.

The viral infection can be a papilloma virus, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, lymphocytic choriomeningitis virus (LCMV), or cancer causing virus. The viral infection can be LCMV.

The method can further include preventing the deleterious effects of an infectious disease in the subject administered the vaccine. This prevention can allow the subject administered the vaccine to survive the infectious disease. In other words, the vaccine affords protection against infectious disease to the subject administered the vaccine. The subject administered the vaccine can have about 90% to about 100% survival of infectious disease, compared to administering the vaccine without ISG15. The subject administered the vaccine can have about 90%, about 91%, about 92%, about 93%, about 94%, about 95%, about 96%, about 97%, about 98%, about 99%, or about 100% survival of infectious disease, compared to administering the vaccine without ISG15.

c. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as a "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Feigner et al., U.S. Pat. No. 5,703,055; Gregoriadis, Liposome Technology, Vols. Ito III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Plymouth Meeting, Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The CELLECTRA device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprise means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

4. Examples

Example 1

Materials and Methods for Examples 2-6

DNA construction and expression: The GenBank accession no. Q64339 for mouse ISG15 was used to synthesize the DNA construct encoding wild-type ISG15 (wtISG15). Mutated ISG15 (mutISG15) is a variant of wtISG15 with point mutations at its C-terminal conjugation site (LRLRGG (SEQ ID NO:12) to AAAAGG (SEQ ID NO:13). All constructs contained highly efficient immunoglobulin E (IgE) leader sequence inserted at the 5' end of the gene. The constructs were commercially synthesized and optimized as described previously in Villarreal D O, Wise M C, Walters J N, Reuschel E L, Choi M J Obeng-Adjei N, et al. Alarmin I L-33 acts as an immunoadjuvant to enhance antigen-specific tumor immunity. Cancer Res 2014; 74:1789-800 (Villarreal et al.) and Shedlock D J, Aviles J, Talbott K T, Wong G, Wu S J, Villarreal D O, et al. Induction of broad cytotoxic T cells by protective DNA vaccination against marburg and ebola. Mol Ther 2013; 21:1432 (Shedlock et al.), which are incorporated by reference in their entirety. HPV16 plasmid containing the E6 and E7 antigens was prepared as previously described in Yan J, ReichenBach D K, Corbitt N, Hokey D A, Ramananthan M P, McKinney K A, et al., Induction of antitumor immunity in vivo following delivery of a novel HPV-16 DNA vaccine encoding an E6/E7 fusion antigen (Yan et al.). Vaccine 2009; 27:431-40, which is incorporated by reference in its entirety. In vitro expression of both ISG15 constructs was confirmed by Western Blot (WB) analysis using. Human rhabdomyosarcoma (RD) cells were maintained in Dulbecco's modified Eagle's medium (Life Technologies, Grand Island N.Y. USA) and supplemented with 10% heat-inactivated fetal calf serum as well as penicillin and streptomycin. After plating $3.0\times10^5$ cells per well, transfection was performed using Neofectin (NeoBiolab Cambridge Mass.) following the manufacture's protocol. Cell were transfected with 2 ug of each DNA construct including pVAX1 empty vector backbone as a negative control. Following 48 hour incubation, cell supernatants were collected and cells were washed with cold PBS. After centrifugation, cells were lysed using cell lysing buffer (Cell Signaling Technology Danvers, Mass.) and EDTA free protease inhibitor cocktail (Sigma-Aldrich St. Louis, Mo.). Cell lysate was run on a 10% Tris-Acetate gel with MES buffer (Life Technologies Grand Island N.Y. USA) and transferred onto a PVDF membrane (Millipore, Darmstadt, Germany). The membrane was block using Odyssey blocking buffer (Licor, Lincoln, Nebr.) for three hours at room temperature followed by probing with rabbit anti-mouse ISG15 (Cell Signaling Technology Danvers, Mass.) and mouse anti-human β-actin (Sigma-Aldrich St. Louis, Mo.) as a loading control at 4° C. overnight. After washing with PBS-Tween, secondary goat anti-mouse IRDye 680RD and goat anti-rabbit IRDye 800 CW (Li-cor, Lincoln, Nebr.) were added for 1 hour at room temperature. The membrane was then washed and imaged on the Odyssey CLX (Licor, Lincoln, Nebr.). In addition, supernatants were also collected at 48 hours after transfection and cytokine secretion was examined by using a CircuLex mouse ISG15 ELISA kit (MBL International), according to manufacturer's protocol. Optical density was measured at 450 nm using a Bioteck EL312e Bio-Kinetics reader (Biotek US, Winooski, Vt.). All supernatants were tested in duplicate with two separate supernatant sample per a plasmid.

Animals: All animals were conducted and maintained in accordance with the NIH and the University of Pennsylvania Institutional Animal Care and Use Committee guidelines. Female C57BL/6 (H-$2^b$) 8-week-old mice and H$2^b$ B6.129S7-Rag1$^{tm1Mom}$/J mice (Rag1 KO) were purchased from Jackson Laboratory.

Animal Immunizations: All mice were immunized intramuscularly (i.m.) in the tibialis anterior muscle. In vivo electroporation (EP) was delivered, with the CELLECTRA adaptive constant current electroporation device (Inovio Pharmaceuticals), at the same site immediately following immunization as previously described in Shedlock et al. The mice were immunized with either 5 μg pVAX1 and 5 μg of HPV16 construct with or without 11 μg of wtISG15 and mutISG15. All studies were repeated at least twice.

ELISPOT Assay: Spleens were harvested and processed 7 days following final immunization as previously described in Villarreal et al. and Shedlock et al. After spleens were harvested and processed, an IFNγ ELISpot assay was performed to determine antigen-specific cytokine secretion from immunized mice as described previously in detail in Villarreal et al., Shedlock et al. and Yan et al. HPV16 Ag-specific T cell responses were measured by stimulating splenocytes with E6 or E7 pooled peptides (2.5 μg/ml final concentration of peptide). The E7 pooled peptide contained the CD8 T cell immunodominant HPV16 D$^b$E7$_{49-57}$ epitope (RAHYNIVTF) from the H-$2^b$ background.

Flow Cytometry: Lymphocytes were isolated and processed from the spleen and peripheral blood as previously described in Villarreal et al., Shedlock et al., and Angelosnato J M, Blackburn S D, Crawford A, Wherry E J. Progressive loss of memory T cell potential and commitment to exhaustion during chronic viral infection. J Virol 2012; 86:8161-70, which is incorporated by reference in its entirety. Lymphocytes were stained with CD8, KLRG1, and MHC class I peptide tetramer to HPV16 H-2D$^b$E7$_{49-57}$ (RAHYNIVTF) (MBL International) as described previously in Villarreal et al. and Duikeren S, Fransen M F, Redeker A, Wieles B, Platenburg G, Krebber W J, et al. Vaccine-induced effector-memory CD8$^+$ T cell responses predict therapeutic efficacy against tumors. J Immunol 2012; 189:3397-403, which is incorporated by reference in its entirety. Intracellular cytokine staining was performed after 5 hours of ex vivo stimulation with the HPV16 E7 peptide DbE7 (RAHYNIVTF) (2.5 μg/ml final concentration of peptide) or E7 pooled peptide to assess CD4 T responses. In cultures being used to measure degranulation, anti-CD107a (FITC; clone 1D4B; Biolegend) was added during time of stimulation to capture the degranulation induced by exposure to stimulation by Ag-specific cells. The cells were then fixed and stained as described elsewhere in Villarreal et al. and Villarreal D O, Walters J, Laddy D J, Yan J, Weiner D B. Multivalent T B vaccines targeting the esx gene family generate potent and broad cell-mediated immune responses superior to BCG. Hum Vaccin Immunother 2014; 10:2188-98, which is incorporated by reference in its entirety. The following antibodies were used for surface staining: LIVE/DEAD Fixable Violet Dead Cell stain kit (Invitrogen), CD4 (FITC; clone RM4-5; ebioscience), CD8 (APC-Cy7; clone 53-6.7; BD Biosciences), NK1.1 (FITC; clone PK136; biolegend); CD49b (FITC; clone DX5; ebioscience). For intracellular staining the following antibodies were used: IFNγ (APC; clone XMG1.2; Biolegend), TNFα (PE; clone MP6-XT22; ebioscience), CD3 (PerCP/Cy5.5; clone 145-2C11; Biolegend); IL-2 (PeCy7; clone JES6-SH4; ebioscience). All data was collected using a LSRII flow cytometer (BD Biosciences) and analyzed using FlowJo software (Tree Star, Ashland, Oreg.) and SPICE v5.3 (free available from http://exon.niaid.nih.gov/spice/). Boolean gating was performed using FlowJo software to examine the polyfunctionality of the T cells from vaccinated animals.

Tumor Cell Line: The TC-1 cell line was a graciously given gift from Dr. Yvonne Paterson of the University of Pennsylvania, Philadelphia, Pa. TC-1 cell line is a well-characterized lung epithelial immortalized cell line, constitutively expresses E6 and E7, and is highly tumorigenic. Briefly, the TC-1 cells were purchased from American Type Culture Collection and cultured as previously described.

In Vivo Therapeutic Study: B6 mice were separated into four groups of 10 mice each and $5\times10^4$ TC-1 cells were subcutaneously implanted into the right flank of each mouse. On day 4, after tumor implantation, each group of mice was immunized intramuscular/electroporation with pVAX1, HPV16, HPV16/wtISg15, HPV16/mutISG15, respectively, and boosted on days 11, 18, and 25. Tumor size was measured using electronic calipers [tumor volume=½ (length×width$^2$)]. Mice were monitored twice a week for tumor growth and were measured as described previously in Villarreal et al. and Yan et al. Under Penn Institutional Animal Care guidelines, mice were sacrificed when tumor size reached 18-20 mm.

In Vivo CD8 T Cell Depletion Study: During therapeutic vaccination, B6 mice were injected intraperitoneally with 200 μg of anti-CD8 (53-6.72, Bio X cell) on day before tumor inoculation and repeated every three days following tumor inoculation. Successful T cell depletion was confirmed by flow cytometric analysis of peripheral blood mononuclear cells.

T-Cell Purification and Adoptive Transfer: CD8 T cells were isolated from splenocytes of vaccinated B6 mice 1 week after final immunization in non-bearing tumor mice (FIG. 2A). For adoptive transfer, ~4×10$^6$ CD8 T cells in 200 μl PBS were injected intravenously via tail vein into each H2$^b$ B6.129S7-Rag1$^{tm1Mom}$/J mouse.

Statistical Analysis: Group analyses were completed by matched, two-tailed, unpaired student's t-tests to analyze statistical significance of all quantitative data produced in this study. A $P<0.05$ was considered statistically significant. Error bars indicate SEM and all tests were per-formed using the Prism Software (*, $P<0.05$; , $P<0.01$; *, $P<0.001$ compared with HPV16 immunization).

Example 2

Design and Expression of ISG15 Constructs

The wild-type ISG15 (wtISG15) adjuvant construct was generated using the mouse ISG15 sequence retrieved from GenBank (accession number: Q64339) with several modifications (FIG. 1A). ISG15 contains a C-terminal LRLRGG motif that is necessary for its conjugation to a variety of target proteins in a process referred to as ISGylation. Therefore, the ISG15 conjugation sequence site was mutated (LRLRGG to AAAAGG) to generate the mutant ISG15 (mutISG15), incapable of conjugation (FIG. 1A). This mutation will assess free ISG15 capability to augment vaccine-induced immunity independent of ISGylation. Both ISG15 constructs were genetically optimized and subcloned into a modified pVAX1 mammalian expression vector (FIG. 1B). To verify the expression of both ISG15 encoding constructs, human rhabdomyosarcoma (RD) cells were transfected separately with each vector and examined by WB. As shown in FIG. 1C, an ~15 kDa free ISG15 was observed for each in cell lysates harvested 48 hours after transfection using anti-ISG15 monoclonal antibody (mAb) for detection. As a negative control, no ISG15 expression could be detected in the pVAX1 group. Next, via an enzyme-linked immunosorbent assay (ELISA) the secretion of free ISG15 was monitored from the cell supernatants that were obtained 48 hours after transfection of RD cells. As projected, supernatants from mutISG15 transfected RD cells had a higher concentration of detectable secreted free ISG15 (7.2 ng/ml), compared to wtISG15 (4.4 ng/ml) (FIG. 1D). This supported the notion that by mutating ISG15's conjugation motif, more unconjugated ISG15 would be available and secreted to the extracellular environment.

Example 3

Immunization with ISG15 Adjuvant Induced Strong HPV E7-specific CD8 T Cell Immune Responses To assess the immunogenicity properties of ISG15, an IFNγ ELISpot assay was used to determine the number of vaccine-induced E7-specific IFNγ secreting cells in response to E7 pooled peptide containing the CD8 immunodominant epitope H-2-D$^b$E7$_{49-57}$ (E7). The immunization regimen is shown in FIG. 2A. Briefly, groups of B6 mice (n=4-5/group) were vaccinated twice at two-week intervals as follows: (i) HPV16 DNA/EP; (ii) HPV16/wtISG15 DNA/EP; (iii) HPV16/mutISG15 DNA/EP; and (iv) pVAX1/EP. The co-administration of HPV16 with wtISG15 resulted in a 3.5-fold increase in the E7-specific IFNγ responses (~230 SFC/million splenocytes) compared with HPV16 alone-immunized group (~66 SFC/million splenocytes). ISG15 is an ubiquitin-like protein that conjugates to target proteins and is critical for control of certain viral and bacterial infections. In addition to the conjugated form of ISG15, it is known, that ISG15 is present in an unconjugated form (free ISG15) and can also play an important role in immunomodulation or during infection. Thus, in the same experiment, we examined if vaccine-induced responses were independent of conjugation by immunizing mice with a mutated form of ISG15 that was free from conjugation. Interestingly, similar to wtISG15, the mutISG15 vaccinated group demonstrated a similar (~4-fold) increase in total E7-specific responses compared with HPV16-only group, suggesting ISG15 can still induce its effects independent of conjugation. Relatively higher induced levels of E6-specific vaccine-induced responses were not found. Together, cytokine-like molecule ISG15 can act as an adjuvant to enhance and stimulate E7-specific Th1-mediated CD8 T cell responses. Moreover, this data demonstrated that the antigen (Ag)-specific responses were most likely attributed by free ISG15.

Example 4

Figure 3:
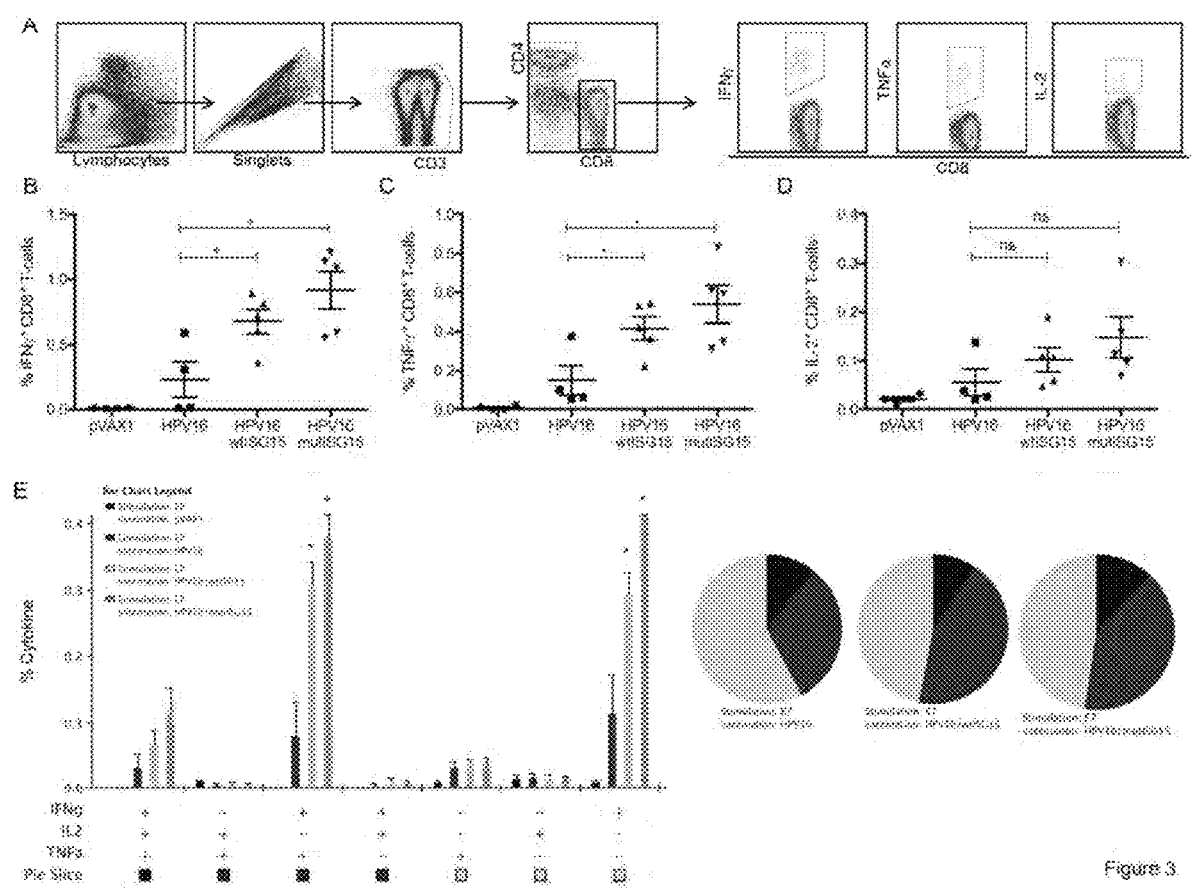
FIG. 3. ISG15 induces polyfunctional HPV16 E7-specific CD8 T cells. (A) Schematic diagram of gating strategy used to identify Ag-specific CD8 T cell populations. (B-D). Column graphs show the percentages of HPV16 E7-specific CD8 T cells releasing total cytokines IFNγ (B), TNFα (C), and IL-2 (D) after stimulation with $D^bE7_{49-57}$-specific peptide. (E) Column chart show polyfunctional subpopulations of single-, double-, or triple-positive CD8 T cells releasing effector cytokines: IFNγ, TNFα, and IL-2 to $E7_{49-57}$-specific stimulation. Pie charts represent proportion of each cytokine population. Experiments were performed at least two times with similar results with 4-5 mice per group. *, P<0.05 compared with HPV16 group. Error bars indicate SEM.
Figure 7:
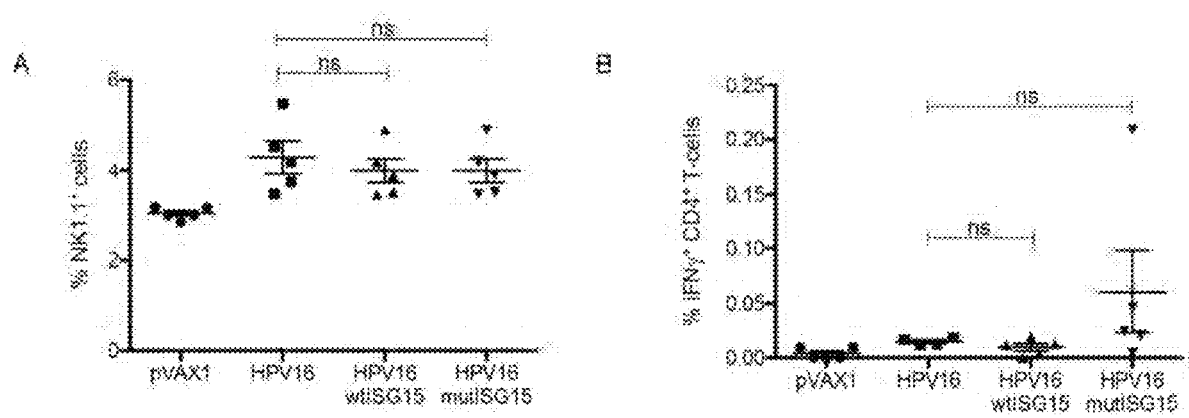
FIG. 7. ISG15 had no profound influence on the NK or CD4 T cells. (A) Dot plot graphs show the percentages of NK cells in the spleens 1 week after final immunization with HPV16, HPV16/wtISG15 or HPV16/mutISG15 groups. (B) Dot graphs show HPV E7-specific CD4 T cells releasing IFNγ in response to ex vivo E7 pooled peptide stimulation in the spleens. Data was not significant. Experiments were performed at least two times (N=4-5 mice/group). *, P<0.05; **, P<0.01. Error bars indicate SEM.

ISG15 Adjuvant Induced Robust Polyfunctional HPV E7-Specific Cell-mediated Responses Considering that CD8$^+$ T cell immune responses are considered essential for facilitating control and elimination of tumors, we further examined the functional profile of E7-specific CD8 T cell populations from vaccinated mice to secrete IFNγ, TNFα and IL-2 in response to D$^b$E7$_{49-57}$ peptide stimulation. The gating strategy for intracellular cytokine multiparametric flow cytometry analysis is shown in FIG. 3A. One week after final vaccination all tested vaccination regimens induced detectable CD8 T cells responses producing all three effector cytokines (FIG. 3). Compared to non-adjuvanted group, both ISG15 vaccine regimens induced substantial E7-specific CD8 T cells producing either total IFNγ (wtISG15, 0.68%; mutISG15, 0.92%) (FIG. 3B) and total TNFα (wtISG15, 0.42%; mutISG15, 0.54%) (FIG. 3C). However, ISG15 only induced a minor increase of Ag-specific CD8 T cells secreting IL-2 (FIG. 3D) Importantly, a significant number of the E7-specific CD8 T cells were polyfunctional, with ISG15 immunized groups eliciting significantly higher frequencies of CD8 T cells producing either IFNγ alone or dual IFNγ$^+$TNFα$^+$ in the spleens 7 days post vaccinations (FIG. 3E). There was also a modest increase in the triple-positive IFNγ$^+$TNFα$^+$IL-2$^+$ CD8 secreting cells in the ISG15-treated groups. Since ISG15 can have an effect on NK cells we monitored the vaccine-induced NK responses. No significant changes were seen after vaccination with ISG15 (FIG. 7A). Furthermore, the administration of ISG15 did not increase vaccine-induced CD4 T cell responses after ex vivo E7 pooled peptide stimulation (FIG. 7B).

Figure 4:
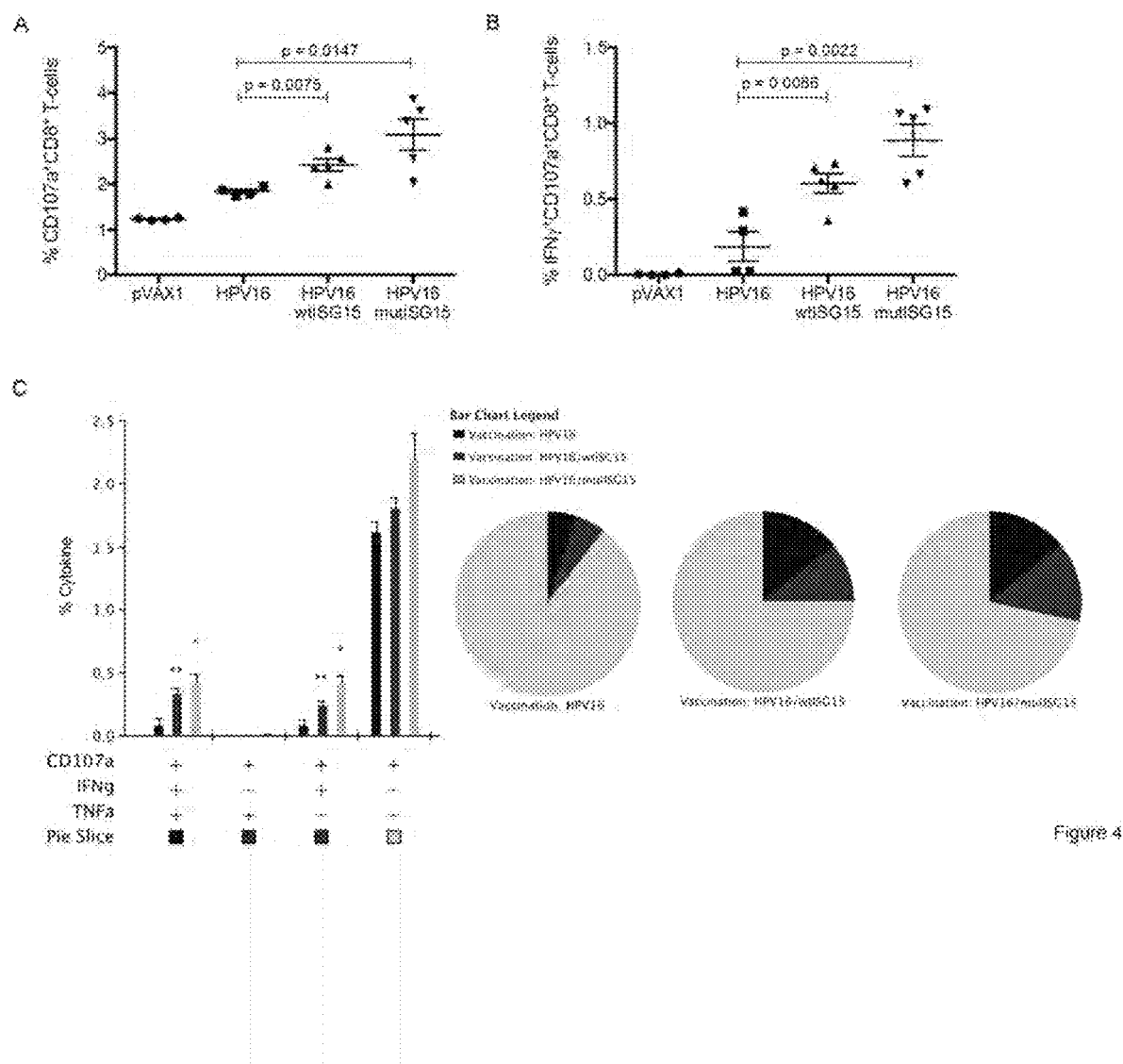
FIG. 4. ISG15 induces HPV16 E7-specific CD8 T cells undergoing cytotoxic degranulation following immunization. E7-specific CD8 T cell responses measured by intracellular cytokine and CD107a staining after stimulation of splenocytes with $D^bE7_{49-57}$ restricted (CD8) peptide were examined in all groups of animals 1 wk after final immunization. (A) Ag-specific cytolytic degranulation of CD8 T cells measured by staining for degranulation marker expression, CD107a. (B and C) Column graph shows the frequency of cytolytic CD8 T cells simultaneously expressing only IFNγ (B) or the frequency of polyfunctional cytokine producing and/or CD107a expressing CD8 T cells (C). Experiments were performed at least twice with similar results with 4-5 mice per group. *, P<0.05; **, P<0.01 compared with HPV16 group. Error bars indicate SEM.
Figure 5:
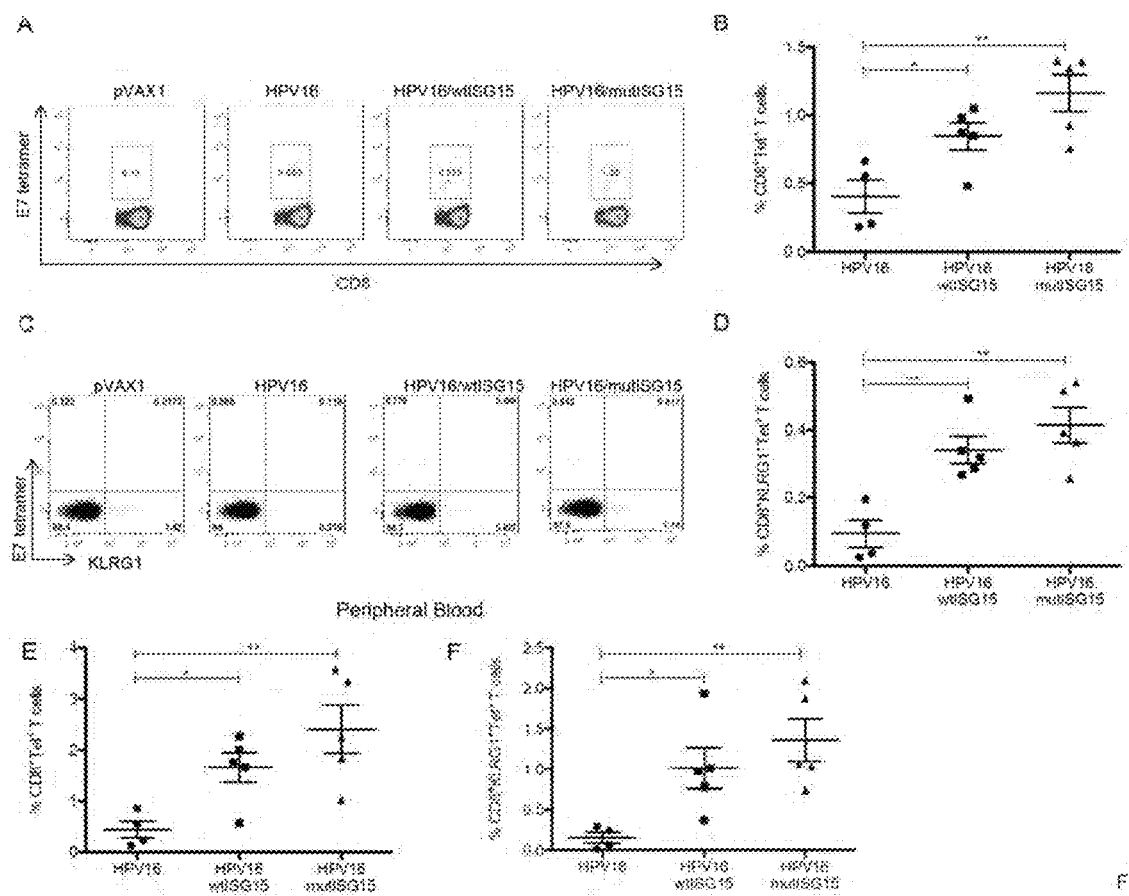
FIG. 5. ISG15 amplify the formation of effector-memory E7-specific CD8 T cells population. Groups B6 mice (n=4-5) were immunized twice with HPV16, HPV16/wtISG15 or HPV16/mutISG15 at two-week intervals. One week after last immunization, both splenocytes and peripheral blood mononuclear cells were strained for CD8, $D^bE7_{49-57}$ tetramer, and the effector memory KLRG1 marker. (A) Representative flow plot showing H2-$D^b$-RAHYNIVTF-restricted HPV16 E7-specific CD8 T cells in the spleen one week after final immunization, or (B) in data represented as a scatter plot graph. (C-D) Representative dot plots (C) or compiled data of the percentages of E7 tetramer-specific memory phenotype population in the spleen (D). (E-F) The percentages of total $D^bE7_{49-57}$ tetramer-binding CD8 T cells from the peripheral blood (E) and tetramer-specific effector memory CD8 T cells (F). Data is representative of at least 2 experiments. *, P<0.05; **, P<0.01. Error bars indicate SEM.

Given that cytotoxic CD8 T lymphocytes (CTL) are critical components in protection, the cytolytic properties of the adjuvant-induced CTL responses to undergo degranulation and secrete effector cytokines simultaneously were assessed (FIG. 5). The groups vaccinated with immunoadjuvant ISG15 showed higher percentages of the degranulation marker, CD107a (wtISG15, 2.4%; mutISG15, 3.1%), compared with HPV16-alone group (FIG. 4A). More interestingly, the HPV16-adjuvanted vaccines elicited substantially higher frequencies of polyfunctional CTLs, with a substantial representation of cells showing one, two, and three immunological functions (FIG. 4B-C). Notably, compared to HPV16 administered alone, the ISG15-treated groups showed significantly higher frequencies of CD8 T cells co-expressing CD107a$^+$ TFN$\gamma^+$ TNF$\alpha^+$ (wtISG15, 0.35%; mutISG15, 0.43%) (FIG. 4C). Collectively, the high frequencies of effector cells secreting antiviral cytokines are indicative of the ISG15 (1) cytokine-like properties, (2) adjuvant effects to enhance vaccine potency and (3) its potential to induce functional effector CTL immunity. Overall, an important observation here was that a DNA plasmid expressing the mutISG15, incapable of conjugation, maintained the adjuvant effects displayed in the wt form, suggesting that ISGylation is likely not required for immunomodulation of CD8 T cells.

Example 5

ISG15 Adjuvant Amplifies Robust Ag-Specific Effector-memory CD8 T Cell Responses The tetramer-specific CD8 T responses that may correlate with vaccine-induced HPV tumor control was also investigated. To this end, non-tumor-bearing B6 mice were immunized with the aforementioned vaccination formulations and schedule in FIG. 2A. One week after final immunization, the magnitude and subset differentiation of Ag-specific CD8 T cell responses were examined using the CD8 epitope specificity of HPV16 E7$_{49-57}$ H2-D$^b$-RAHYNIVTF tetramer in the spleens and blood (FIG. 5). Both wtISG15 and mutISG15 constructs were able to markedly increase the D$^b$E7 tetramer-specific CD8 T cell responses in the spleen compared to HPV16 group alone (FIGS. 5A and B). In addition, the delivery of both ISG15 plasmids also significantly amplified the number of D$^b$E7 tetramer-specific CD8 T cells in the peripheral blood, inferring tumor trafficking of tumor target-specific CTL's (FIG. 5E). The frequency of E7-tetramer T cells in the blood within the wtISG15 and mutISG15 groups were 4- to 5.5-fold higher compared with the nonadjuvanted group, respectively. This data confirmed that immunoadjuvant ISG15 can amplify the Ag-specific CD8 T cells.

It has been suggested that effector-memory CD8 T cells are optimal subsets for protective immunity and may predict therapeutic efficacy against tumors. Effector memory T cells are the focus of cancer vaccines as they can initiate rapid effector function and migrate quickly to the infected- or tumor-site. In this study, the D$^b$E7 MHC class I tetramer vaccine-induced effector/effector-memory CD8$^+$ T cell subset based on expression marker of KLRG1 (effector memory—T$_{eff}$) was measured (FIG. 5). The administration of wtISG15 resulted in a ~3-fold increase in the percentages of T$_{eff}$ cells in the spleen, compared with the HPV16-only vaccinated group (FIGS. 5C and D). Similarly, the inclusion of mutISG15 also markedly enhanced the T$_{eff}$ responses in the spleen (FIG. 5D). In addition, as shown in FIG. 5F, the percentages of T$_{eff}$ cells in the blood were significantly higher in the adjuvant groups. These data suggest that immunoadjuvant ISG15 can enhance the magnitude and quality of E7-specific CD8 T cell responses.

Example 6

Figure 6:
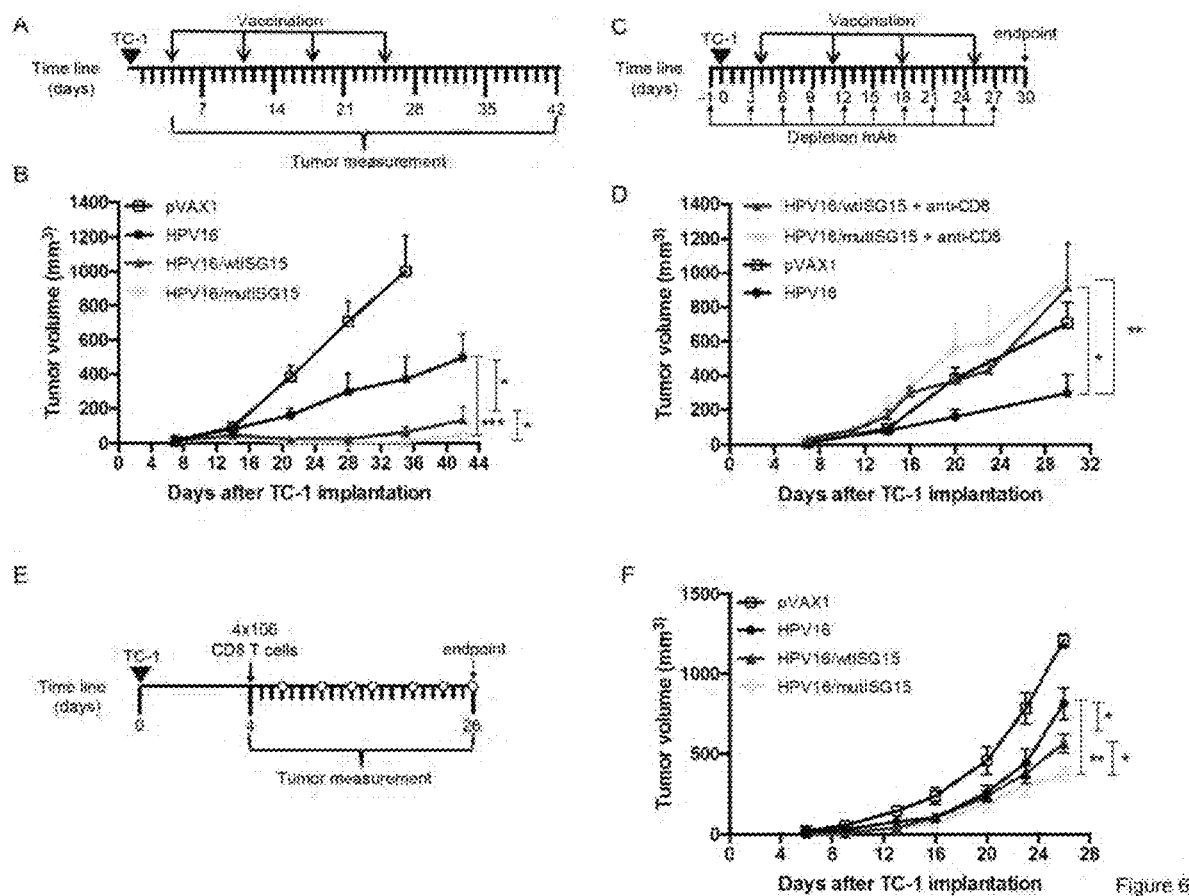
FIG. 6. The therapeutic effects induced by ISG15 in tumor-bearing mice. (A) Schematic representation for therapeutic study. (B) Tumor growth measurement after therapeutic DNA/EP vaccination (n=10). (C) Schematic representation for CD8 T cell depletion with therapeutic vaccination. (D) Tumor growth curve of vaccinated groups (n=5) without CD8 T cells. (E and F) schematic representation for T cell adoptive transfer study (E). Approximately $4\times10^6$ CD8 T cells from vaccinated mice were purified from splenocytes and adoptively transferred into tumor-bearing T cell immunodeficient B6 Rag1 KO mice (n=5) and assessed for tumor growth (F). All tumor-bearing mice were injected subcutaneously with $5\times10^4$ TC-1 cells. *, P<0.05; , P<0.01; *, P<0.001. Error bars indicate SEM.
Figure 8:
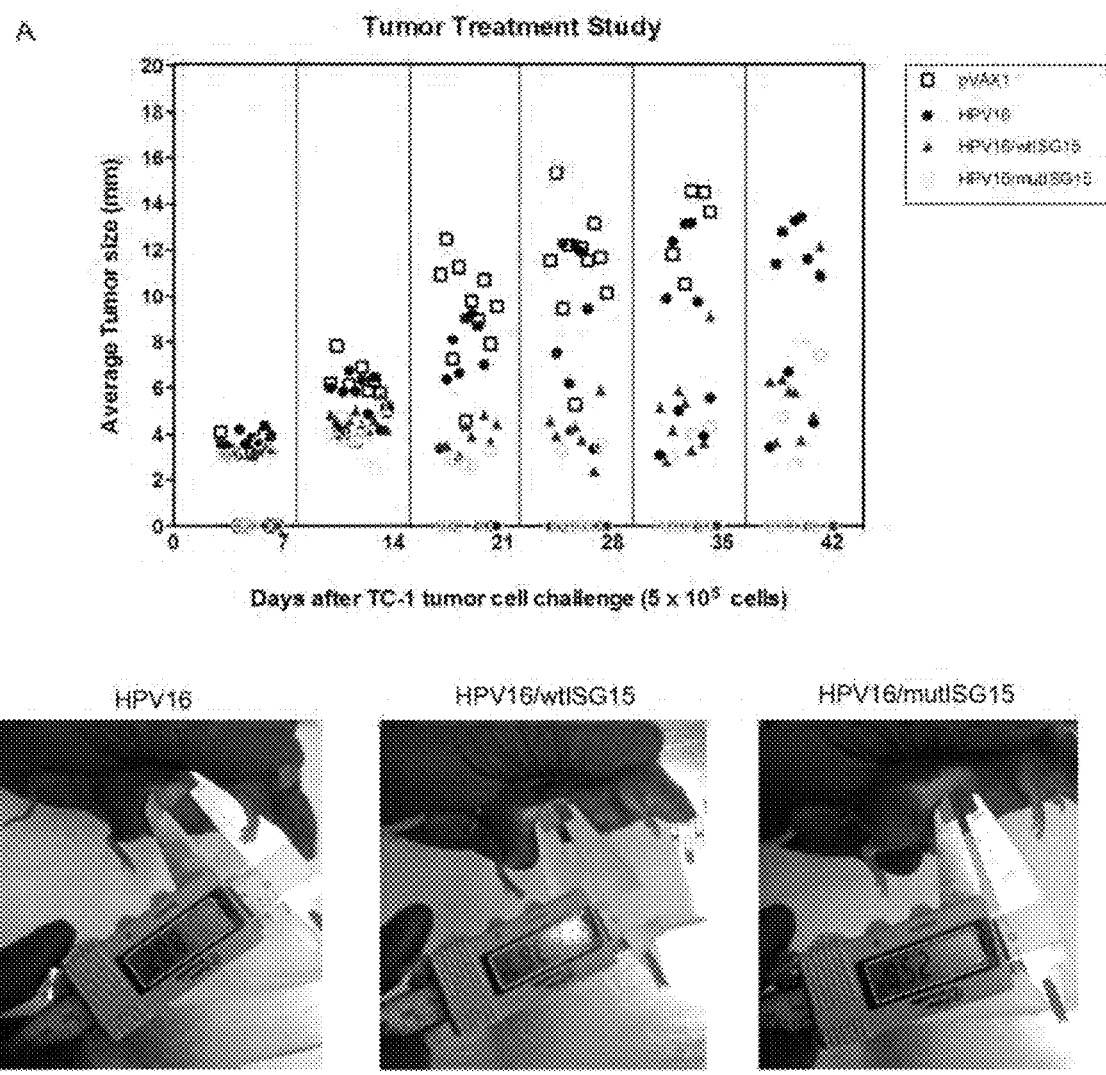
FIG. 8. Inclusion of ISG15 as a vaccine adjuvant improves both tumor control and regression in tumor-bearing mice. Groups of C57Bl/6 mice (n=10/group) were injected subcutaneously with $5\times10^4$ TC-1 cells. Starting on day 4 after tumor implantation, all groups of mice were immunized followed with three boosts at weekly intervals. Immunization with ISG15 constructs delayed tumor growth or led to tumor regression in tumor-bearing mice. Tumor measurements (average values for each individual mice) for each time point are shown only for surviving mice. Mice were sacrificed when tumor diameter reached approximately 18-20 mm. Images are representative examples of tumor size at day 42 after tumor implantation.

ISG15 Acted as an Effective CD8 T Cell Immunoadjuvant Inducing Antitumor Immunity The therapeutic efficacy of ISG15 in a TC-1 tumor-bearing mice model was next investigated. Naïve recipient B6 mice (n=10/group) were first inoculated subcutaneously with TC-1 tumor (5×10$^4$) cells followed by HPV16, HPV16/wtISG15, HPV16/mutISG15 or pVAX1 vaccination four days after tumor implantation (tumors had reached an average size of 2 mm), followed with three boosts at 1-week intervals (FIG. 6A). Tumors in mice immunized with the mixture of HPV16/wtISG15 grew significantly slower than HPV16 vaccinated group alone (FIG. 6B). In contrast, pVAX1 control group failed to show any therapeutic effect with all mice dying by day 35. Interestingly, mice given the HPV16/mutISG15 significantly induced better tumor control than mice given HPV16/wtISG15, likely due to inducing higher CTL responses. In addition, compared to HPV16/wtISG15, the HPV16/mutISG15 combination rapidly induced regression of more established TC-1 tumors (FIG. 8). At day 42 post tumor implantation, 6/10 mice in the HPV16-mutISG15 were tumor free, compared with either HPV16 (1/10) or HPV16-wtISG15 (2/10) (FIG. 8). Taken together, the adjuvant properties of ISG15 demonstrated effective control and therapeutic cure of HPV tumor-bearing mice.

Given ISG15 adjuvant properties to enhance E7-specific-CTL responses that are essential to target established pre-existing HPV infections, the important role of ISG15-elicited CD8 T cells for HPV TC-1 tumor elimination was investigated. Therefore, in the therapeutic setting, CD8 T cells were depleted by intraperitoneally injection of commercial anti-CD8 antibody, starting 1 day before tumor inoculation and repeated every three days after tumor implantation (FIG. 6C). The results revealed CD8 depletion significantly abrogates the therapeutic effects of ISG15 adjuvant, and all mice died <30 days (FIG. 6D). To confirm these findings, CD8 T cell adoptive transfer experiments in T cell immunodeficient B6 Rag1 KO mice were performed. 4×10$^6$ CD8 T cells purified from splenocytes of HPV16, HPV16/wtISG15, and HPV16/mutISG15 immunized mice (FIG. 2A) were injected intravenously 4 days post-inoculation of TC-1 cells (FIG. 6E). As compared to HPV16 and naive controls, mice that received either wtISG15 or mutISG15 vaccine-induced CD8 T cells, resulted in substantial slower tumor growth (FIG. 6F), likely owing to their functional CTL phenotype (FIGS. 3 and 4). Taken together, ISG15-elicited CD8 T cells proved essential in prolonging survival and controlling tumor growth in the HPV TC-1 therapeutic model.

Examples 1-6 demonstrate the therapeutic efficacy of ISG15 immunoadjuvant properties to augment Ag-specific CD8 T cell tumor immunity. A preclinical HPV therapeutic challenge model was used to test the adjuvant effects of ISG15 in a DNA vaccine setting. The main results of this study are that inclusion of ISG15 can (i) increase the polyfunctional Ag-specific CTL responses; (ii) induce effector-like memory CD8 T cell subset differentiation; (iii) have antitumor therapeutic effects; and (iv) elicit vaccine-induced protective immunity independent of conjugation, further establishing free ISG15 cytokine-like properties.

Example 7

Materials and Methods for Example 8-10

Mice: ISG15−/− mice and their syngeneic wild-type strain C57BL/6J were obtained from Jackson Laboratory (Bar Harbor, Me.) and bred and housed in the University of Pennsylvania Hill Pavilion Animal Facility and in the TTUHSC Abilene LARC. Mice were kept on a 12-hour light/dark cycle with sterile water and UV-treated or autoclaved standard rodent diet. All mouse experiments were performed in accordance with the regulations of the Institutional Animal Care and Use Committee of the TTUHSC and University of Pennsylvania according to the guidelines of the National Institute of Health.

Bacterial Strains: LM strain 10403 S was cultured in BHI (Brain-heart infusion, CM1135, Oxoid LTD, Hampshire, England) media supplemented with 50 ug/mL of streptomycin, harvested at mid-log growth phase (0.6-0.8 at O.D. 600), aliquots flash-frozen in liquid $N_2$, and stored at −80° C. LM stock titers were determined by serial dilution of a thawed stock vial, plating of dilutions onto BHI-streptomycin agar plates, and counting the colony-forming units (CFUs) after 18-24 hrs. at 37° C. For each infection experiment, a frozen stock vial was freshly thawed, bacteria pelleted by centrifugation, and the pellet washed twice with 1× phosphate-buffered saline (PBS).

In Vitro LM Infection: Infection of bone marrow-derived macrophage (BMM) was performed as described previously in Singh, R., A. Jamieson, and P. Cresswell, GILT is a critical host factor for *Listeria monocytogenes* infection. Nature, 2008. 455(7217): p. 1244-7 (Singh et al.), which is incorporated by reference in its entirety. For mRNA analysis, BMMs were seeded onto tissue culture-treated dishes, incubated overnight, and infected with LM at a multiplicity of infection (MOI) of 10. The infected cells were washed, gentamicin was added 30 min after infection, and cells processed for RNA isolation using the RNeasy Mini kit (Qiagen) according to the manufacturer's instructions.

In Vivo LM Infection: For primary infection studies to determine cytokine responses by qPCR and ELISA, 6-8 week old C57BL/6 and ISG15−/− mice were euthanized three days after intraperitoneal (i.p.) injection with $10^5$ CFU of LM in 200p1 of sterile 1×PBS. To determine the role of ISG15 in poly(I:C)-exacerbated listeriosis, C57BL/6J and ISG15$^{-/-}$ mice were infected i.p. with $10^4$ CFUs of LM alone or administered 150 µg of poly(I:C) i.p. two days after LM infection. All mice were euthanized on day 4 post-infection and spleens extracted. Spleens were processed into single-cell suspensions, serially diluted, plated onto BHI-agar plates supplemented with 50 ug/mL streptomycin and colony-forming units counted after overnight growth at 37° C. For longitudinal infection studies, 6-8 week old C57BL/6J and ISG15$^{-/-}$ mice were i.p. injected with $10^4$ CFUs of LM in 200 µl of sterile 1×PBS. At experiment end, mice were euthanized and processed for bacterial load. LM CFUs in the spleen and liver were determined as described previously in Singh et al. In FIG. 1, mice were injected with $10^3$, $10^4$, and $10^5$ CFU LM in 200µl of 1×PBS i.p. and euthanized at day 4-post infection. Spleens and livers of the infected mice were harvested and LM bacterial load determined by serial dilution of single cell suspensions and colony-forming units counted after overnight growth on BHI-agar supplemented with 50 ug/mL streptomycin. In FIG. 2, 6-8 week old C57BL/6 and ISG15−/− mice were infected with $10^3$ CFU of the attenuated Aacta LM strain, DPL-4029. These mice along with naïve WT and ISG15−/− mice were subsequently challenged with intraperitoneal injection of $10^5$ CFUs LM. Five days after challenge, mice were euthanized and organs processed for flow cytometric analyses and bacterial load determination Quantitative PCR: RNA was isolated from splenocytes and bone marrow-derived macrophage using an RNeasy plus mini kit (Qiagen). RNA was quantified using a Nanodrop spectrophotometer and 1 ug of RNA was converted to cDNA using the High Capacity cDNA Reverse Transcription Kit (Applied Biosystems). The Step One Plus Real Time system from Life Technologies was used for qPCR analysis in combination with FAST SYBR Green (Applied Biosystems). To determine relative quantity of target genes between groups, 18S rRNA was used as a reference.

ELISA: Serum was collected by post-euthanasia heart puncture bleeds and blood clots removed after incubation at 4° C. for 30 minutes followed by centrifugation. Serum samples were diluted 1:40 and assayed for levels of IFN-γ using the mouse ELISA Ready-SET-Go! kit (eBiosciences, San Diego, Calif., USA) according to the manufacturer's instructions. Results were obtained at O.D. 450 using a Micro-plate reader (SynergyHT, BioTek) and analyzed on Gen5 (Ver1.08).

Figure 2:
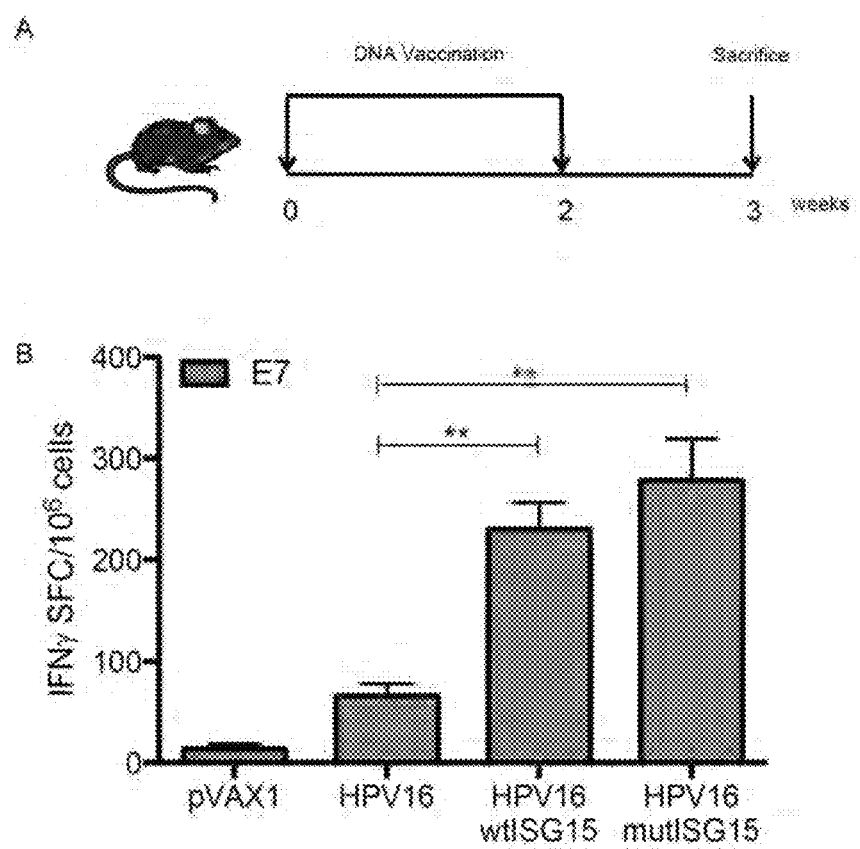
FIG. 2. Co-delivery of ISG15 DNA vaccination promoted E7-specific CD8 T cell immune responses secreting IFNγ production. (A) Immunization schedule for DNA vaccine adjuvant study. C57BL/6 mice (n=4-5/group) were immunized twice at two-week intervals with HPV16 construct with or without wtISG15 or mutISG15 adjuvant constructs via IM/EP delivery. One week after last vaccination, spleens were harvested to analyze the Ag-specific CD8 T cell responses. (B) The frequency of E7-specific IFNγ (spot forming cells/$10^6$ splenocytes) responses induced after each vaccination was determined by IFNγ ELISpot assay in response to E7 pooled peptide containing the specific CD8 HPV16 E7 epitope (RAHYNIVTF (SEQ ID NO:11)). Data represent 2 independent experiments with 4-5 mice per group. *, P<0.05; **, P<0.01. Error bars indicate SEM.

Flow Cytometric Analysis: In FIG. 1-2, spleens were extracted from mice and placed in 5 mL complete media (Corning Cellgro; DMEM 1×; Cat no. 15-013-CM). Spleens were mechanically macerated and passed through 40 um cell strainers (Fisher, Cat no. 22363549, 22363547) to produce single-cell suspensions. Cells were treated with ACK lysis buffer for 3-5 minutes at room temperature and washed three times in 1×PBS. Cells were suspended in complete media and cell counts determined using a Beckman Coulter Vi-Cell XR. For T cell stimulation, $2\times10^6$ cells were plated in 96-well round-bottom plates and stimulated with 5 ug/mL of peptide or PMA/ionomycin for 6 hours at 37° C., 5% $CO_2$ in the presence of monensin. For cell surface staining, splenocytes were stained for various cell surface markers after Fc-blockade with anti-CD16/CD32(Clone 93; 14-0161-85) using fluorochrome-labeled mAbs. All samples were acquired on an LSRII or LSRFortessa flow cytometer (Becton Dickinson Biosciences, San Jose, Calif., USA), and data was analyzed using FlowJo software (v10, Tree Star). In FIG. 3, splenocytes were added to a 96-well plate ($1\times10^6$/well) and were stimulated with the LCMV immunodominant LCMV epitope from the H-$2^b$ background ($D^bNP_{396-404}$ (NP396)) (Invitrogen) for 5-6 hours at 37 C/5% $CO_2$ in the presence of Protein Transport Inhibitor Cocktail (Brefeldin A and Monensin) (eBioscience) according to the manufacturer's instructions. The Cell Stimulation Cocktail (plus protein transport inhibitors) (phorbol 12-myristate 13-acetate (PMA), ionomycin, brefeldin A and monensin) (eBioscience) was used as a positive control and R10 media as negative control. All cells were then stained for surface and intracellular proteins as described by the manufacturer's instructions (BD, San Diego, Calif.). Briefly, the cells were washed in FACS buffer (PBS containing 0.1% sodium azide and 1% FCS) before surface staining with flourochrome-conjugated antibodies. Cells were washed with FACS buffer, fixed and permeabilized using the BD Cytofix/Cytoperm™ (BD, San Diego, Calif., USA) according to the manufacturer's protocol followed by intracellular staining. All data was collected using a LSRII flow cytometer (BD Biosciences) and analyzed using FlowJo software (Tree Star, Ashland, Oreg.) and SPICE v5.2 (free available from http://exon.niaid.nih.gov/spice/). Boolean gating was performed using FlowJo software to examine the polyfunctionality of the T cells from vaccinated animals. Dead cells were removed by gating on a LIVE/DEAD fixable violet dead cell stain kit (Invitrogen) versus forward scatter (FSC-A).

Plasmid Construction: The GenBank accession no. Q64339.4 for mouse ISG15 was used to synthesize the ISG15 plasmid DNA construct. The ISG15 plasmid DNA construct has a highly efficient immunoglobulin E (IgE) leader sequence inserted at the 5'end of the gene. The construct was commercially synthesized and genetically optimized (codon- and RNA-optimization) for expression in mice and then subcloned (all by GenScript, Piscataway, N.J.) into a modified pVAX1 mammalian expression vector (Invitrogen, Carlsbad, Calif.). Plasmid expressing pLCMV-NP (NP) was prepared as previously described in Shedlock, D. J., et al., A highly optimized DNA vaccine confers complete protective immunity against high-dose lethal lymphocytic choriomeningitis virus challenge. Vaccine, 2011. 29(39): p. 6755-62 (Shedlock 2013 et al.), which is incorporated by reference in its entirety.

Transfection and Expression of Plasmids: In vitro ISG15 was confirmed by western blot (WB) analysis. 293T cells were cultured in a 6-well plate and transfected with construct using Neofectin transfection reagent (NeoBiolab) following manufacturer's protocol. Forty-eight hours later, cells were lysed using modified cell lysis buffer (Cell Signaling) with complete protease inhibitor cocktail tablets (Roche) and cell lysate was collected. WB analysis was performed with an anti-ISG15 antibody (Cell Signaling) and visualized with IRDye 800CW goat anti-rabbit antibody (Li-Cor) using the Odyssey imagining system (Li-Cor). β-actin served as a loading control and visualized with IRDye 680 goat anti-mouse antibody (Li-Cor). In addition, an indirect immunofluorescence microscopy assay was also executed to confirm expression of ISG15 DNA construct. Rhabdomyosarcoma (RD) cells were plated on two-well chamber slides (BD Biosciences) and grown to 70% confluence overnight in a 37 incubator with 5% $CO_2$. The cells were transfected with 1 μg of IL-33 constructs and the control plasmid pVAX (1 μg/well) using TurboFectin™8.0 Transfection Reagent (OriGene) according to the manufacturer's instructions. Forty-eight hours later the cells were fixed on slides using ice cold methanol for 10 min. The cells were stained with anti-ISG15 mouse monoclonal antibody (Cell Signaling) and subsequently incubated with Alexa 555-conjugated anti-rat secondary antibody (Cell Signaling). Slides were mounted using Fluoromount G with DAPI (Southern Biotechnology). Images were analyzed by florescence microscopy (Leica DM4000B, Leica Microsystems Inc, USA) and quantification was conducted using SPOT Advanced software program (SPOT™ Diagnostic Instruments, Inc).

Vaccinations and LCMV Challenge: Mice were immunized once intramuscularly (i.m.) in the tibialis anterior muscle as previously described in Villarreal et al. and Shedlock et al. In vivo Electroporation was delivered, with the CELLECTRA adaptive constant current electroporation device (Inovio Pharmaceuticals), at the same site immediately following vaccination. The mice (n=5) were immunized with either 10 μg pVAX1 or 10 μg pLCMV-NP with or without 11 μg of ISG15 construct. All studies were repeated at least three times. For lethal challenge studies, mice were challenged i.c. with 40×$LD_{50}$ of LCMV Armstrong as previously described in Shedlock 2013 et al. in 30 μl of virus diluent (PBS with 20% FBS and 1×Anti-Anti (Invitrogen, Carlsbad, Calif.). All mice LCMV challenged were housed in a BSL-2 facility and were observed daily for 21 days.

ELISpot Assays: Spleens were harvested 21 days following immunization to monitor vaccine-induced responses as previously described in Villarreal et al. and Shedlock et al. After spleens were harvested and processed, IFN-γ ELISpot assays were performed to determine the antigen-specific cytokine secretion from immunized mice as described previously in Villarreal et al. and Shedlock et al.

Statistical Analysis: The student t test was applied for comparison of the quantitative data of the cellular immune responses induced by infection or vaccination. Statistically significant outliers were removed from datasets by application of the ROUT method. All error bars indicate SEM and all tests were performed using the Prism Software (La Jolla, Calif.) (*, $P<0.05$; , $P<0.01$; *, $P<0.001$ compared with NP). Survival curves were analyzed by log-rank (Mantel-Cox) test.

Example 8

Effect of ISG15 on the Innate Immune Response

To determine the relevance of ISG15 in the innate immune response to the model pathogen, *Listeria monocytogenes* (LM), ISG15 gene expression was examined after LM infection in wild-type C57/BL6 mice. Mice were infected were infected with $10^5$ LM CFUs and euthanized at the peak of infection on day 3 along with a group of uninfected mice. Spleens were excised, processed into a single-cell suspension, and RNA extracted. After conversion to cDNA, spleens were assessed for expression of Isg15 by qPCR analysis. Bone marrow-derived macrophage (BMM) were differentiated with M-CSF and infected with LM (n=3/group). BMM were lysed after 8 and 16 hours post-infection along with uninfected controls and processed for RNA extraction. After cDNA conversion, BMMs were assessed for Isg15 gene expression along with the gene for its E1-activating enzyme, Ube1l. Wild-type (n=4) and ISG15−/− mice (n=5) infected with $10^5$ LM CFUs were euthanized on day 3 post-infection and serum collected to assess levels of secreted ISG15 protein by ISG15 ELISA. BMMs were infected with LM followed by treatment with isotype control or IFN-beta blockading antibody one hour post-infection (n=3/group). At experiment end, BMMs were lysed, mRNA extracted, converted to cDNA, and Isg15 gene expression assessed by qPCR analysis. Wild type (n=4) and ISG15−/− (n=5) mice were infected i.p. with $10^4$ CFUs of LM alone or administered 150 μg of poly(I:C) i.p. two days after LM infection (n=3/group). All mice were euthanized on day 4 post-infection and spleens excised and processed into single-cell suspensions. Suspensions were serially diluted and plated out on BHI-streptomycin agar plates in order to determine colony-forming units (CFUs) per spleen. Wild-type and ISG15−/− mice (n=3/group) were infected i.p. with $10^4$ CFUs of LM and euthanized on day 1, 3, and 5 post-infection. Spleens and livers from infected mice were excised and processed into single-cell suspensions. Suspensions were serially diluted and plated out on BHI-streptomycin agar plates in order to determine colony-forming units (CFUs) per organ. Total bacterial load determined by adding LM CFUs from the spleen and liver of each mouse. In order to determine if susceptibility to LM infection is dose-dependent, WT and ISG15−/− mice (n=5/group) were infected i.p. with a log range of doses of LM CFUs. At day 4 post-infection, spleens and livers were extracted, processed into single-cell suspensions, serially diluted, and plated out on BHI-streptomycin agar plates. Scatter plots depicting LM CFUs in the spleens of WT and ISG15−/− after infection with a log range of doses were prepared. Scatter plots depicting LM CFUs in the livers of wild-type and ISG15−/− after infection with a log range of doses were also prepared. Wild-type (n=5/group) and ISG15−/− mice (n=3/group) were infected i.p. with $10^5$ CFUs of LM and euthanized at the peak of infection on day 3 post-infection. Spleens were excised, processed into single-cell suspensions, and RNA extracted. After conversion to cDNA, spleens were assessed for expression of the proinflammatory cytokine gene Ifng. Production and secretion of IFN-γ was confirmed by ELISA analysis of serum from WT and ISG15−/− mice (n=5/group) infected with $10^5$ CFUs LM at peak of infection on day 3 post-infection. Amount of IFN-γ protein in serum was calculated with a protein standard. *, $P<0.05$; , $P<0.01$; *, $P<0.001$.

Isg15 mRNA expression was significantly induced at the peak of infection on day 3, with 100-fold higher expression of Isg15 in the spleen, a major site of infection, compared to uninfected control mice. Infection of bone marrow-derived macrophages (BMM) with LM also resulted in a temporal induction of Isg15 and the gene encoding the ISG15 E1 conjugating enzyme, Ube1L. Furthermore, secreted ISG15 protein could be detected in the serum of infected WT mice at the peak of LM infection but not in ISG15−/− controls. Expression of Isg15 during LM infection was Type I IFN-dependent as antibody-mediated blockade of IFN-β significantly blunted the Isg15 induction in LM-infected BMMs (FIG. 1D). These data suggest the ISG15 pathway is induced during LM infection and is dependent on production of Type I IFN. In contrast to viral infection, Type I IFN exacerbates certain bacterial infections including listeriosis by impairing both innate and adaptive responses to LM. To determine if ISG15 mediates Type I IFN exacerbation of listeriosis, ISG15−/− mice were infected with LM and Type I IFN was induced by administering a dsRNA mimetic molecule, poly (I:C). Surprisingly, ISG15 is not necessary for Type I IFN-mediated exacerbation of listeriosis and two independent experiments suggested that ISG15−/− mice may even be more susceptible to LM infection. The role of ISG15 in innate immunity to LM was further explored with a time-course infection. On day 1 post-infection, ISG15−/− mice were more resistant to acute infection with LM as evidenced by significantly reduced bacterial burden. However, bacterial burden was significantly elevated in ISG15−/− mice at the peak of infection on day 3 and continued to rise subsequently in contrast to their wild-type counterparts. Whether this result was only relevant at the initial infection dose, $10^4$ CFUs, was determined next, as previous studies have shown dose-dependent susceptibility to LM. WT and ISG15−/− mice were infected with a log range of infection doses from $10^3$ CFUs to $10^5$ CFUs of LM. In the spleens of WT mice receiving the lowest dose of LM ($10^3$ CFUs), only 40% of mice had evidence of listeriosis. However, 80% of ISG15$^{-/-}$ mice had detectable levels of LM in their spleen. Similar results were observed in the livers of WT and ISG15−/− after receiving the lowest dose with 20% and 100% of mice demonstrating listeriosis, respectively. Significantly increased listeriosis was also observed at higher starting doses in both the spleens and livers of ISG15−/− mice. While NK cells numbers were similar (FIG. 11), the increased susceptibility to acute LM infection in ISG15−/− mice did correlate with significantly reduced expression of splenic ifng and serum levels of IFN-γ, an essential proinflammatory cytokine in the clearance of LM infection.

Example 9

Effect of ISG15 on the Adaptive Immune Response

As LM virulence has previously been reported to inversely correlate with adaptive immunity to LM, it was determined whether ISG15 deficiency compromised adaptive immune responses to LM. Wild-type (WT) and ISG15−/− mice were infected i.p. with $10^5$ CFUs of LM with or without prior infection with $10^3$ CFUs of the attenuated LM strain, DPL-4029. LLO-specific IFNγ-producing splenic CD4$^+$ T cells from LM-infected WT and ISG15−/− mice with and without stimulation with phorbol 12-myristate 13-acetate (PMA) (50 ng/mL) and ionomycin (800 ng/mL) were identified and analyzed. Splenic CD8+ T cell numbers and splenic CD4$^+$ T cells during innate and adaptive response to LM were identified and analyzed. Total LM bacterial burden in the mouse, in the spleen, and liver, of WT and ISG15−/− mice was analyzed. Splenic myeloid cells during innate and adaptive response to LM were identified and analyzed. The percentage of myeloid cells that are CD11 $C^{hi}$ and overall percentage of splenocytes that are conventional DCs during LM infection. WT and ISG15−/− spleens were stimulated with 1 ug of LPS for 6 hrs. and surface expression of markers associated with DC maturation were assessed by flow cytometry for expression of CD86, CD80, and co-expression of CD80 and CD86. *, $P<0.05$; , $P<0.01$; *, $P<0.001$; ****, $P<0.0001$.

After prior infection with a highly attenuated strain of LM (DPL-4029), WT and ISG15−/− mice were challenged with the virulent 10403 S strain of LM and development of adaptive immunity assessed on day 5 post-infection. ISG15−/− mice generated similar numbers of LLO-specific splenic CD4+ T cells after LM challenge. Additionally, overall numbers of splenic CD4+ and CD8+ cells were comparable between WT and ISG15−/− mice. However, ISG15−/− mice appeared to mount a less effective adaptive immune to response to LM when overall bacterial load was assessed. Interestingly, these defects were tissue-specific as splenic LM bacterial load in previously infected mice was comparable between ISG15−/− and WT mice, in agreement with the splenic T cell numbers. However, liver bacterial load in previously infected ISG15−/− mice was approximately 100-fold greater than in previously infected WT mice (FIG. 2G). While this result suggests ISG15 could be involved in liver immune-privilege, other factors may also be at play. The altered adaptive immune response to LM may be due to defects observed in the myeloid compartment, as greater numbers of myeloid cells were observed in the spleens of ISG15−/− mice but there were significantly fewer conventional dendritic cells to facilitate induction of a robust T cell response to the liver. Furthermore, stimulation of splenic dendritic cells with LPS revealed that ISG15 deficiency impairs dendritic cell maturation as evidenced by reduced surface levels of costimulatory molecules CD80 and CD86. These results suggest that ISG15 may be important in fostering T cell-mediated adaptive immunity by augmenting antigen-presenting cell number and function.

Example 10

Effect of ISG15 as an Adjuvant to Augment Immune Response

To determine if these observed immunoregulatory properties of ISG15 could be leveraged therapeutically to enhance responses to immune-privileged sites, overexpression of ISG15 in wild-type mice was induced by delivering it as DNA vaccine adjuvant to augment T cell-mediated immunity. Expression of ISG15 in 293 T cells as examined by Western blot analysis. Protein was detected by anti-ISG15 mAb, and expression of ISG15 was detected via immunofluorescence microscopy. Secretion of ISG15 after transfection of empty pVAX and pVAX-mISG15 in 3T3 cells (n=3/group) was confirmed via ELISA of conditioned media. B6 mice (n=5/group) were immunized once with or without ISG15. 21 days later, mice were sacrificed and spleens were processed to monitor the vaccine induced immune responses. IFN-γ ELISpot were performed to detect antigen specific immune responses to the LCMV DbNP396-404 antigen (NP396) in combination with ISG15 when used in IM immunization via electroporation. Multiparameter flow cytometry was used to determine the percentages of polyfunctional CD8+ T cell cytokine profile. The percentage of NP-specific CD8+ T cells was displayed as triple, double of single positive CD8+ T cells secreting cytokines. Pie charts were generated and show the relative proportion of each cytokine subpopulation. Mice (n=10/group) were immunized one time IM using EP with bug of empty vector control plasmid (pVAX) or bug of LCMV-NP with or without ISG15 adjuvant. At day 21 post-vaccination, mice were challenged intracranial with 40×LD50 LCMV and animal survival was analyzed. Experiments were performed at least three times in independent experiments. *, $P<0.05$; , $P<0.01$, **, $P<0.0001$.

The in vivo mammalian ISG15 expression DNA plasmid was developed. Briefly, the mouse ISG15 gene was cloned into the pVAX mammalian expression vector under control of a CMV promoter and with an IgE leader sequence to allow for secretion. After transfection of 293T cells with pVAX-mISG15, cells proficiently expressed intracellular murine ISG15 as determined by Western Blot analysis and fluorescent microscopy. As previously documented, ISG15 protein was found in both the cytoplasm and nucleus as determined by colocalization with the nuclear stain, DAPI (FIG. 3C). Due to the inclusion of an IgE leader sequence, transfection with pVAX-mISG15 also resulted in proficient secretion of mouse ISG15 into the culture supernatants from pVAX-mISG15 transfected 3T3 cells in comparison to empty vector transfected cells. To determine if ISG15 could be leveraged therapeutically to augment CD8+ T cell-mediated immunity, further studies were performed with an infection model that ISG15 is not relevant, the intracranial (i.c.) lymphocytic choriomeningitis virus (LMCV) infection model. The LCMV infection model is an established model to study CD8+ T cell responses to the brain of infected mice. Therefore, to characterize the CD8+ T cell responses driven by ISG15, groups of mice were intramuscularly administered plasmid expressing LCMV structural protein, NP, with or without plasmid expressing mISG15. Mice receiving the NP vaccine administered with mISG15 generated significantly more $D^bNP_{396-40}$ (NP396)-specific IFN-γ spot-forming cells (SFCs) than mice receiving pVAX-NP or empty pVAX plasmid alone. Furthermore, the NP vaccine administered with mISG15 induced significantly higher percentages of NP-specific polyfunctional CD8+ T cells compared to mice receiving vector expressing antigen alone. To determine if the observed adjuvant effect of mISG15 impacted survival, mice were challenged 21 days after vaccination with a lethal intracranial dose ($40 \times LD_{50}$) of the LCMV Armstrong strain. Dramatically increased survival to lethal LCMV infection was observed in the mISG15 and NP vaccine group compared to the group-receiving NP antigen alone (FIG. 3G). Taken together, these data demonstrate that mISG15 can act as an immunoadjuvant to activate highly effective antigen-specific CD8+ T-cell responses to even immune-privileged sites.

The studies of Examples 7-10 support an expanded role of ISG15 in immunity, as it has been found that it is involved in innate immunity to the bacterial pathogen, LM. Furthermore, while ISG15 deficiency does not hinder formation of splenic LM-specific T cell responses, protective adaptive immunity is not evident in the liver of ISG15−/− mice after subsequent LM challenge. Additionally, splenic DCs from ISG15−/− mice have reduced expression of maturation markers and overexpression of ISG15 by WT mice was able to augment pathogen-specific CD8+ T cell responses and increase survival to lethal intracranial LCMV challenge. Examples 7-10 indicate ISG15 as a critical mediator of innate anti-bacterial immunity and a potent activator of adaptive immunity.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A vaccine comprising an antigen and ISG15.

Clause 2. The vaccine of clause 1, wherein ISG15 is encoded by a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, a nucleotide sequence as set forth in SEQ ID NO:3, a nucleotide sequence having at least about 95% identity to a nucleotide sequence as set forth in SEQ ID NO:5, a nucleotide sequence as set forth in SEQ ID NO:5, a nucleotide sequence having at least about 95% identity to a nucleotide sequence as set forth in SEQ ID NO:7, a nucleotide sequence as set forth in SEQ ID NO:7, a nucleotide sequence having at least about 95% identity to a nucleotide sequence as set forth in SEQ ID NO:9, and a nucleotide sequence as set forth in SEQ ID NO:9.

Clause 3. The vaccine of clause 2, wherein ISG15 is encoded by the nucleotide sequence as set forth in SEQ ID NO:1.

Clause 4. The vaccine of clause 2, wherein ISG15 is encoded by the nucleotide sequence as set forth in SEQ ID NO:3.

Clause 5. The vaccine of clause 2, wherein ISG15 is encoded by the nucleotide sequence as set forth in SEQ ID NO:5.

Clause 6. The vaccine of clause 2, wherein ISG15 is encoded by the nucleotide sequence as set forth in SEQ ID NO:7.

Clause 7. The vaccine of clause 2, wherein ISG15 is encoded by the nucleotide sequence as set forth in SEQ ID NO:9.

Clause 8. The vaccine of clause 1, wherein the antigen is encoded by a first nucleic acid and ISG15 is encoded by a second nucleic acid.

Clause 9. The vaccine of clause 1, wherein the antigen is selected from the group consisting of: a human papilloma virus (HPV) antigen, an Human Immunodeficiency Virus (HIV) antigen, an influenza antigen, a *Plasmodium falciparum* antigen, a *Mycobacterium tuberculosis* antigen, a lymphocytic choriomeningitis (LCMV) antigen, and a fragment thereof.

Clause 10. The vaccine of clause 9, wherein the HPV antigen is selected from the group consisting of: HPV16 E6 antigen, HPV16 E7 antigen, and a combination thereof.

Clause 11. The vaccine of clause 9, wherein the HIV antigen is selected from the group consisting of: Env A, Env B, Env C, Env D, B Nef-Rev, Gag, and any combination thereof.

Clause 12. The vaccine of clause 9, wherein the influenza antigen is selected from the group consisting of: H1 HA, H2 HA, H3 HA, H5 HA, BHA antigen, and any combination thereof.

Clause 13. The vaccine of clause 9, wherein the *Plasmodium falciparum* antigen includes a circumsporozoite (CS) antigen.

Clause 14. The vaccine of clause 9, wherein the *Mycobacterium tuberculosis* antigen is selected from the group consisting of: Ag85A, Ag85B, EsxA, EsxB, EsxC, EsxD, EsxE, EsxF, EsxH, EsxO, EsxQ, EsxR, EsxS, EsxT, EsxU, EsxV, EsxW, and any combination thereof.

Clause 15. The vaccine of clause 9, wherein the LCMV antigen is selected from the group consisting of: nucleoprotein (NP), glycoprotein (GP), and a combination thereof.

Clause 16. The vaccine of clause 1, further comprising a pharmaceutically acceptable excipient.

Clause 17. The vaccine of clause 8, wherein the second nucleic acid further comprises an expression vector.

Clause 18. A method for increasing an immune response in a subject in need thereof, the method comprising administering the vaccine of clause 1 or 2 to the subject.

Clause 19. The method of clause 18, wherein administering the vaccine includes electroporation.

Clause 20. The method of clause 18, wherein the immune response in the subject is increased by at least about 2-fold, compared to administering a vaccine without ISG15.

Clause 21. The method of clause 20, wherein the immune response in the subject is increased by at least about 4-fold, compared to administering a vaccine without ISG15.

Clause 22. The method of clause 21, wherein increasing the immune response in the subject includes increasing a cellular immune response in the subject.

Clause 23. A method for treating cancer in a subject in need thereof, the method comprising administering the vaccine of clause 1 or 2 to the subject.

Clause 24. The method of clause 23, further comprising reducing tumor size by at least 10% in the subject, compared to administering a vaccine without ISG15.

Clause 25. The method of clause 23, further comprising increasing tumor regression by at least 10% in the subject, compared to administering a vaccine without ISG15.

Clause 26. The method of clause 23, wherein the cancer is selected from the group consisting of: an HPV-associated cancer, an HBV-associated cancer, an ovarian cancer, a prostate cancer, a breast cancer, a brain cancer, a head and neck cancer, a throat cancer, a lung cancer, a liver cancer, a cancer of the pancreas, a kidney cancer, a bone cancer, a melanoma, a metastatic cancer, an hTERT-associated cancer, a FAP-antigen associated cancer, a non-small cell lung cancer, a blood cancer, an esophageal squamous cell carcinoma, a cervical cancer, a bladder cancer, a colorectal cancer, a gastric cancer, an anal cancer, a synovial carcinoma, a testicular cancer, a recurrent respiratory papillomatosis, a skin cancer, a glioblastoma, a hepatocarcinoma, a stomach cancer, an acute myeloid leukemia, a triple-negative breast cancer, and a primary cutaneous T cell lymphoma.

Clause 27. The method of clause 23, wherein the cancer is the HPV-associated cancer.

Clause 28. A nucleic acid molecule comprising one or more nucleotide sequences selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, a nucleotide sequence as set forth in SEQ ID NO:3, a nucleotide sequence having at least about 95% identity to a nucleotide sequence as set forth in SEQ ID NO:5, a nucleotide sequence as set forth in SEQ ID NO:5, a nucleotide sequence having at least about 95% identity to a nucleotide sequence as set forth in SEQ ID NO:7, a nucleotide sequence as set forth in SEQ ID NO:7, a nucleotide sequence having at least about 95% identity to a nucleotide sequence as set forth in SEQ ID NO:9, a nucleotide sequence as set forth in SEQ ID NO:9, and any combination thereof.

Clause 29. The nucleic acid molecule of clause 28, wherein the nucleic acid molecule is a plasmid.

Clause 30. The nucleic acid molecule of clause 28, wherein the nucleic acid molecule is one or more plasmids.

Clause 31. The vaccine of clause 8, further comprising an antigen peptide encoded by one of SEQ ID NO:1, SEQ ID NO:3, SEQ ID NO:5, SEQ ID NO:7, or SEQ ID NO:9.

Clause 32. The vaccine of clause 31, further comprising an ISG15 peptide encoded by one of SEQ ID NO:2, SEQ ID NO:4, SEQ ID NO:6, SEQ ID NO:8, or SEQ ID NO:10.

What is claimed is:

1. A vaccine comprising:
   a) an antigen, a nucleic acid molecule encoding an antigen, or a combination thereof; and
   b) a nucleic acid molecule comprising a nucleotide sequence encoding ISG15, wherein the nucleotide sequence encoding ISG15 comprises one or more nucleotide sequences selected from the group consisting of a nucleotide sequence having at least about 95% identity to the nucleotide sequence as set forth in SEQ ID NO:5 and the nucleotide sequence as set forth in SEQ ID NO:5.

2. The vaccine of claim 1, wherein the antigen is encoded by a first nucleic acid and ISG15 is encoded by a second nucleic acid.

3. The vaccine of claim 1, wherein the antigen is selected from the group consisting of: a human papilloma virus (HPV) antigen, an Human Immunodeficiency Virus (HIV) antigen, an influenza antigen, a Plasmodium falciparum antigen, a Mycobacterium tuberculosis antigen, a lymphocytic choriomeningitis (LCMV) antigen, and an immunogenic fragment thereof.

4. The vaccine of claim 3, wherein the HPV antigen is selected from the group consisting of: HPV16 E6 antigen, HPV16 E7 antigen, and a combination thereof.

5. The vaccine of claim 3, wherein the HIV antigen is selected from the group consisting of: Env A, Env B, Env C, Env D, B Nef-Rev, Gag, and any combination thereof.

6. The vaccine of claim 3, wherein the influenza antigen is selected from the group consisting of: H1 HA, H2 HA, H3 HA, H5 HA, BHA antigen, and any combination thereof.

7. The vaccine of claim 3, wherein the Plasmodium falciparum antigen includes a circumsporozoite (CS) antigen.

8. The vaccine of claim 3, wherein the Mycobacterium tuberculosis antigen is selected from the group consisting of: Ag85A, Ag85B, EsxA, EsxB, EsxC, EsxD, EsxE, EsxF, EsxH, EsxO, EsxQ, EsxR, EsxS, EsxT, EsxU, EsxV, EsxW, and any combination thereof.

9. The vaccine of claim 3, wherein the LCMV antigen is selected from the group consisting of: nucleoprotein (NP), glycoprotein (GP), and a combination thereof.

10. The vaccine of claim 1, further comprising a pharmaceutically acceptable excipient.

11. The vaccine of claim 2, wherein the second nucleic acid further comprises an expression vector.

12. A nucleic acid molecule comprising one or more nucleotide sequences selected from the group consisting of: a nucleotide sequence having at least about 95% identity to the nucleotide sequence as set forth in SEQ ID NO:5, and the nucleotide sequence as set forth in SEQ ID NO:5.

13. The nucleic acid molecule of claim 12, wherein the nucleic acid molecule is a plasmid.

14. The nucleic acid molecule of claim 12, wherein the nucleic acid molecule is one or more plasmids.

15. The vaccine of claim 2, wherein the vaccine further comprises an antigen peptide encoded by a nucleic acid comprising the nucleotide sequence as set forth in SEQ ID NO:5.

16. The vaccine of claim 15, wherein the antigen peptide is an ISG15 peptide comprising the amino acid sequence as set forth in SEQ ID NO:6.

* * * * *